US011458010B2

(12) United States Patent
Lissy

(10) Patent No.: US 11,458,010 B2
(45) Date of Patent: Oct. 4, 2022

(54) MEDICAL HOLDING SYSTEM AND METHOD FOR FACILITATING THE PREPARATION OF IMPLANTABLE ELEMENTS

(71) Applicant: United Health Services Hospitals, Inc., Binghamton, NY (US)

(72) Inventor: Micah E. Lissy, Vestal, NY (US)

(73) Assignee: United Health Services Hospitals, Inc., Binghamton, NY (US)

( * ) Notice: Subject to any disclaimer, the term of this patent is extended or adjusted under 35 U.S.C. 154(b) by 309 days.

(21) Appl. No.: 16/385,427

(22) Filed: Apr. 16, 2019

(65) Prior Publication Data

US 2019/0314141 A1 Oct. 17, 2019

Related U.S. Application Data

(60) Provisional application No. 62/658,053, filed on Apr. 16, 2018.

(51) Int. Cl.
*A61F 2/08* (2006.01)
*A61B 90/57* (2016.01)
*A61B 17/04* (2006.01)

(52) U.S. Cl.
CPC ............ *A61F 2/0805* (2013.01); *A61B 90/57* (2016.02); *A61F 2/0811* (2013.01); *A61B 17/04* (2013.01); *A61F 2002/0852* (2013.01)

(58) Field of Classification Search
CPC .. A61F 2/0805; A61F 2002/0852; A61F 2/08; A61F 2/0811; A61F 2220/0075; A61B 90/50; A61B 17/28; A61B 2017/00526; A61B 17/04; A61B 2090/508; A61B 17/56; A61B 17/08; A61B 17/32; A61B 17/0401

USPC ....................................................... 623/13.11
See application file for complete search history.

(56) References Cited

U.S. PATENT DOCUMENTS

| | | | |
|---|---|---|---|
| 5,298,012 A | 3/1994 | Handlos | |
| 5,415,651 A | 5/1995 | Schmieding | |
| 5,683,400 A | 11/1997 | McGuire | |
| 6,001,106 A | 12/1999 | Ryan et al. | |
| 6,547,778 B1 | 4/2003 | Sklar et al. | |

(Continued)

FOREIGN PATENT DOCUMENTS

| | | |
|---|---|---|
| EP | 1297798 A2 | 4/2003 |
| EP | 2772193 A1 | 9/2014 |
| EP | 2923672 A1 | 9/2015 |

OTHER PUBLICATIONS

PCT/US2019/027614; filed Apr. 16, 2019; International Search Report and Written Opinion; dated Jul. 10, 2019; 11 pages.

(Continued)

*Primary Examiner* — Mohamed G Gabr
(74) *Attorney, Agent, or Firm* — Barclay Damon LLP

(57) ABSTRACT

A medical holding system and method are disclosed herein. The medical holding system, in an embodiment, includes a holder and a support device. The holder includes a grasper configured to be coupled to an end of an implantable element. The holder also includes a coupler having a coupler portion. The support device includes a release interface. The holder and the support device are configured to keep the implantable element suspended above a support surface throughout engagement and disengagement conditions of the coupler portion.

20 Claims, 34 Drawing Sheets

(56) References Cited

U.S. PATENT DOCUMENTS

| | | | |
|---|---|---|---|
| 7,118,578 | B2 | 10/2006 | West, Jr. et al. |
| 8,298,284 | B2 | 10/2012 | Cassani |
| 8,439,976 | B2 | 5/2013 | Albertorio et al. |
| 2002/0040240 | A1 | 4/2002 | Heckele et al. |
| 2005/0065533 | A1 | 3/2005 | Magen et al. |
| 2011/0287403 | A1 | 11/2011 | Ciccone, II et al. |
| 2016/0008123 | A1 | 1/2016 | Woodruff et al. |
| 2016/0045305 | A1* | 2/2016 | Eaton .................. A61B 17/15 606/88 |
| 2018/0013252 | A1* | 1/2018 | Moser .................. B23K 3/087 |
| 2018/0050407 | A1* | 2/2018 | Richards ............ H01R 43/0263 |

OTHER PUBLICATIONS

PCT/US2019/027614; International Filing Date Apr. 16, 2019; International Preliminary Report on Patentability; dated Oct. 29, 2020 (10 pages).

Arthrex, Inc.; Arthrex SpeedWhip Technique with FiberLoop; Jun. 11, 2010; retrieved from the Internet: <https://www.arthrex.com/resources/animation/sjjf3PkEEeCRTQBQVoRHOw/speedwhip-technique-with-fiberloop>; 5 pages.

Arthrex, Inc.; Arthrex SpeedWhip Video; Aug. 14, 2017; retrieved from the Internet: <https://www.youtube.com/watch?v=SFfkNRac2_U>; 7 pages.

Plasma Engineer; Something Surprising Blog; Feynman's Shaft Passer; Nov. 9, 2011; retrieved from the Internet: <http://somethingsurprising.blogspot.com/2011/11/feynmans-shaft-passer-in-reality.html>; 4 pages.

Arthrex, Inc.; GraftPro™, Graft Preparation System; On or before Dec. 31, 2016; 4 pages.

Wikipedia; Shaft Passer by Wilipedia, Dec. 5, 2017; retrieved from the Internet: <https://en.wikipedia.org/wiki/Shaft_passer>; 4 pages.

Arthrex, Inc.; SpeedWhip™ Technique with FiberLoop® and TigerLoop®; On or before Dec. 31, 2011; 1 page.

Vunoo; Printable Cable Passer; Nov. 30, 2013; retrieved from the Internet: <https://www.thingiverse.com/make:55132>; 2 pages.

PCT/US2021/026969; filed Apr. 13, 2021; International Search Report and Written Opinion; dated Jul. 12, 2021 (17 pages).

EP Application No. 19788911; filed Apr. 16, 2019; Extended Search Report; dated Dec. 20, 2021 (9 pages).

* cited by examiner

MEDICAL HOLDING SYSTEM AND METHOD FOR FACILITATING THE PREPARATION OF IMPLANTABLE ELEMENTS

CROSS-REFERENCE TO RELATED APPLICATION

This application is a non-provisional of, and claims the benefit and priority of, U.S. Provisional Patent Application No. 62/658,053 filed on Apr. 16, 2018. The entire contents of such application are hereby incorporated herein by reference.

BACKGROUND

In certain surgical procedures, the surgeon inserts or implants a graft into the surgical site of the patient. Depending upon the type of surgery, the graft can be tissue excised from the patient or tissue supplied from a donor. In some cases, the graft must be prepared or treated before the surgery. In surgeries involving the repair or replacement of tendons or ligaments, the graft can include a substitute tendon or substitute ligament.

As illustrated in FIGS. 1-2, there are known graft preparation stations 10, 12 designed to hold one or more grafts 14, 15. Each of these stations 10, 12 has one or more left posts 16, 17 and one or more right posts 18, 19. To suspend the graft 14, the user can couple ropes 20, 22 to the left and right posts 17, 19, respectively. To suspend the graft 15, the user can couple the graft 15 directly to the left post 16, and the user can use rope 23 to couple the graft 15 to the right post 18.

Consequently, as illustrated in FIG. 2, there is an uninterrupted, continuous line 26 (whether a line of graft by itself or a line made of graft and rope) extending between the posts 16, 18 or between posts 17, 19. This continuous line 26 acts as a barrier that restricts the types of graft preparation methods that can be employed. For example, this continuous line 26 prevents the user from using a loop-based suturing method, such as the FiberLoop® and TigerLoop® suturing methods published by Arthrex, Inc. As illustrated in FIG. 3, a loop-based suturing method can involve the use of a needle 28 connected to a loop of rope or a looped rope 30. According to this suturing method, the user must periodically pass the looped rope 30 over the end of the graft 14 to be treated. However, the continuous line 26 prevents this passage, and, therefore, the known graft preparation stations 10, 12 impede, or are incompatible with, the use of loop-based suturing methods.

Because of this problem, clinicians have had to resort to a relatively complex, labor intensive process for the use of loop-based suturing methods. The labor intensive process requires at least two people, typically a surgeon and a physician assistant or other clinical assistant. For example, as shown in FIGS. 4-9, the labor intensive process involves the following steps:
  (a) a surgeon 32 locks a surgical clamp 34 onto the treatable end 36 of the graft 38, as shown in FIG. 4;
  (b) the assistant 40 holds the surgical clamp 34, as shown in FIG. 4, using the assistant's upper hand 42;
  (c) after the surgeon 32 passes the needle (not shown) through the treatable end 36 of the graft 38, the surgeon 32 moves the looped rope 30 beyond the clamp handles 46, as shown in FIG. 4;
  (d) the assistant 40 then moves the surgical clamp 34 upward, partially through the opening 41 defined by the looped rope 30, as shown in FIG. 4;
  (e) as the surgeon 32 moves the looped rope 30 upward, the upper hand 42 of the assistant 40 releases the surgical clamp 34, and the lower hand 48 of the assistant 40 grasps the surgical clamp 34, as shown in FIG. 5;
  (f) the assistant 40 then clears away the upper hand 42, enabling the surgeon 32 to pass the looped rope 30 over the surgical clamp 34, as shown in FIG. 6,
  (g) the surgeon 32 then proceeds to suture the treatable end 36, as shown in FIGS. 7-9, by passing the needle 28 through the treatable end 36; and
  (h) the assistant 40 and surgeon 32 repeat the foregoing steps (b) through (g) multiple times to fully suture the treatable end 36.

This labor intensive process can be prone to error, is tedious, is time consuming and is complex, resulting in fatigue of the surgeon and clinical assistant. These factors can expose the surgeon and assistant to heightened risks of graft preparation errors, deficiencies in the graft preparation, needle pricks and injuries, and other disadvantages.

The foregoing background describes some, but not necessarily all, of the problems, disadvantages, shortcomings and challenges related to the preparation of implantable elements.

SUMMARY

The medical holding system, in an embodiment, includes a holder and a support device. The holder includes a grasper and a coupler. The grasper is configured to be coupled to an implantable element. The implantable element includes a first element end configured to be suspended by a first upright support. The first upright support is configured to be supported by a support surface. The implantable element also includes a second element end. The grasper is configured to be secured to the second element end of the implantable element. The coupler includes a coupler portion. The support device is configured to be coupled to the support surface. The support device includes a second upright support. The second upright support includes a release interface.

The coupler portion and the release interface are configured to cooperate with each other so that coupler portion is configured to be transitioned from an engagement condition to a disengagement condition and back to the engagement condition. In the engagement condition, the coupler portion is engaged with the release interface to keep the implantable element suspended above the support surface when the implantable element is subject to a suturing force that acts downward toward the support surface. In the disengagement condition, the coupler portion is disengaged from the release interface in response to a pass-through force, thereby forming a passageway between the support device and the second element end. The passageway is configured to receive a cord segment of a medical looped cord. After the cord segment passes through the passageway, the coupler portion is configured to transition back to the engagement condition. The coupler portion and the release interface are configured to keep the implantable element suspended above the support surface throughout the engagement and disengagement conditions.

In another embodiment, the medical holding system includes a holder and a support device. The holder includes a grasper and a coupler. The grasper is configured to be coupled to an end of an implantable element when the implantable element includes an opposing end coupled to an upright support. The coupler includes a coupler portion. The support device includes a release interface. The support device is configured to be supported by a support surface. The holder and the support device are configured to cooperate with each other so that the coupler portion is configured to transition from an engagement condition to a disengagement condition and back to the engagement condition. In the engagement condition, the coupler portion is engaged with the release interface. In the disengagement condition, the coupler portion is disengaged from the release interface in response to a pass-through force, thereby forming a passageway between the support device and the end of the implantable element. The passageway is configured to receive a cord segment of a medical cord. The holder and the support device are configured to keep the implantable element suspended above the support surface throughout the engagement and disengagement conditions.

The medical holding system is configured to be manufactured according to a manufacturing method. In an embodiment, the manufacturing method includes: configuring, structuring or fabricating a holder. The configuring, structuring or fabricating of the holder includes configuring, structuring or fabricating a grasper to be coupled to an end of an implantable element when the implantable element includes an opposing end coupled to an upright support. The configuring, structuring or fabricating of the holder also includes configuring, structuring or fabricating a coupler to include a coupler portion. The manufacturing method also includes configuring, structuring or fabricating a support device to include a release interface and to be supported by a support surface. Also, the manufacturing method includes configuring, structuring or fabricating the holder and the support device to cooperate with each other so that the coupler portion is operable to transition from an engagement condition to a disengagement condition and back to the engagement condition. In the engagement condition, the coupler portion is engaged with the release interface. In the disengagement condition, the coupler portion is disengaged from the release interface in response to a pass-through force, thereby forming a passageway between the support device and the end of the implantable element. The passageway is configured to receive a cord segment of a medical cord. The holder and the support device are configured to keep the implantable element suspended above the support surface throughout the engagement and disengagement conditions.

Additional features and advantages of the present disclosure are described in, and will be apparent from, the following Brief Description of the Drawings and Detailed Description.

DETAILED DESCRIPTION

Figure 1:
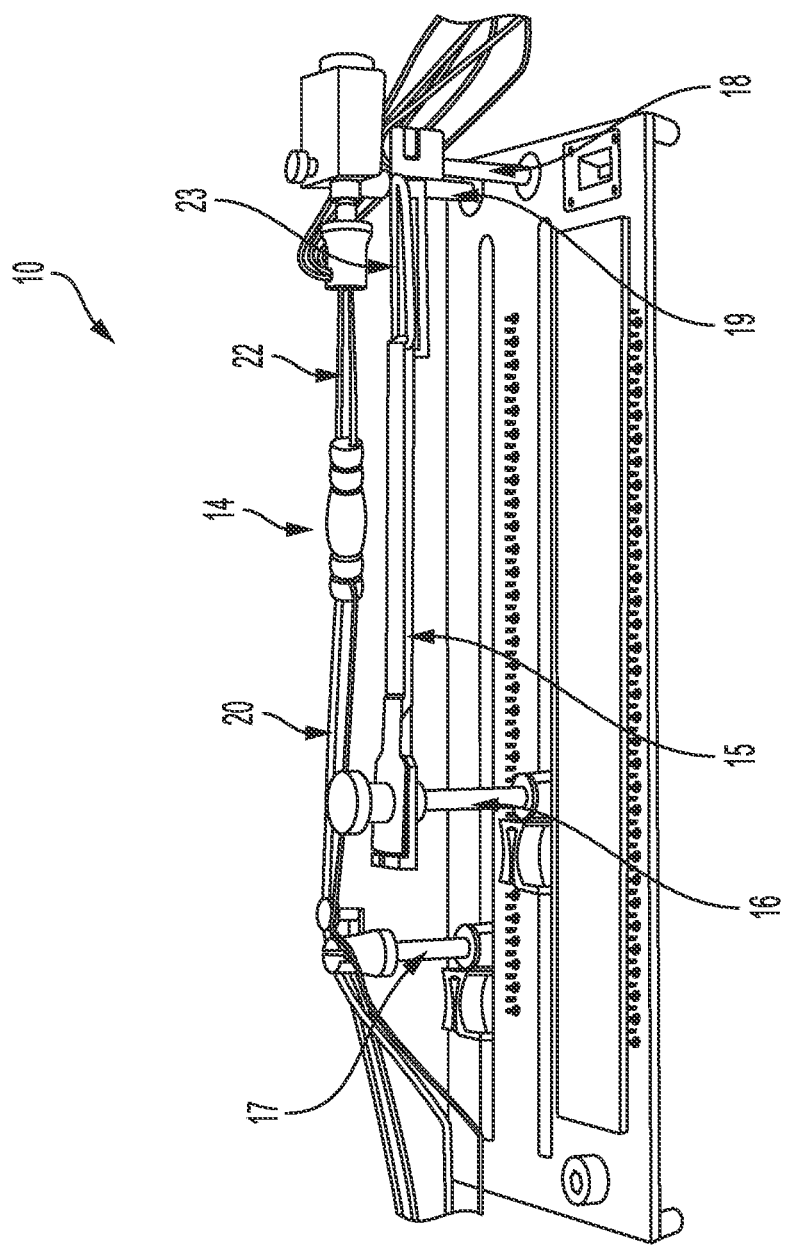
FIG. 1 is an isometric view of a prior art graft preparation station.
Figure 2:
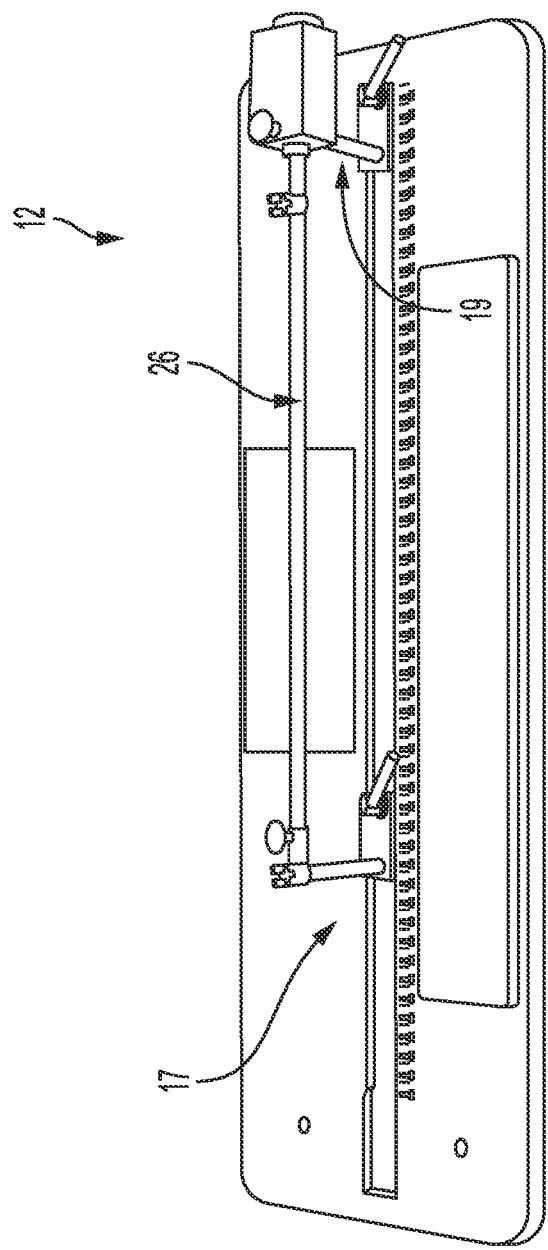
FIG. 2 is an isometric view of another prior art graft preparation station.
Figure 3:
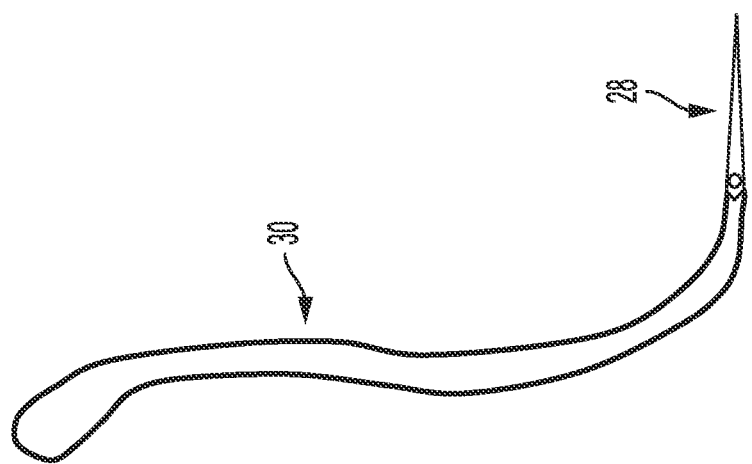
FIG. 3 is a top view of a prior art looped rope and needle.
Figure 4:
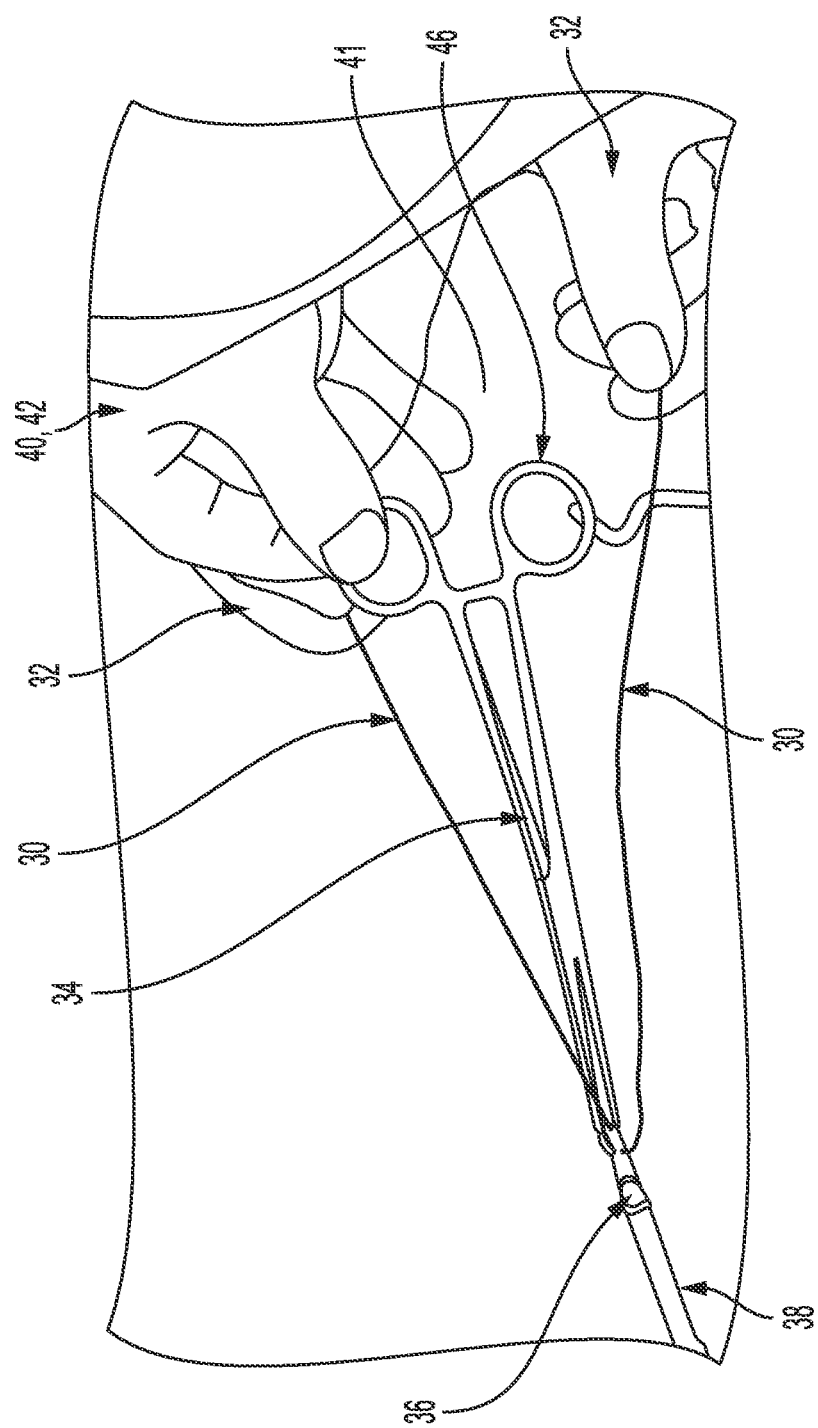
FIG. 4 is an isometric view of a prior art looped rope, as held in the first step of an example of a prior art labor intensive process for the use of a loop-based suturing method.
Figure 5:
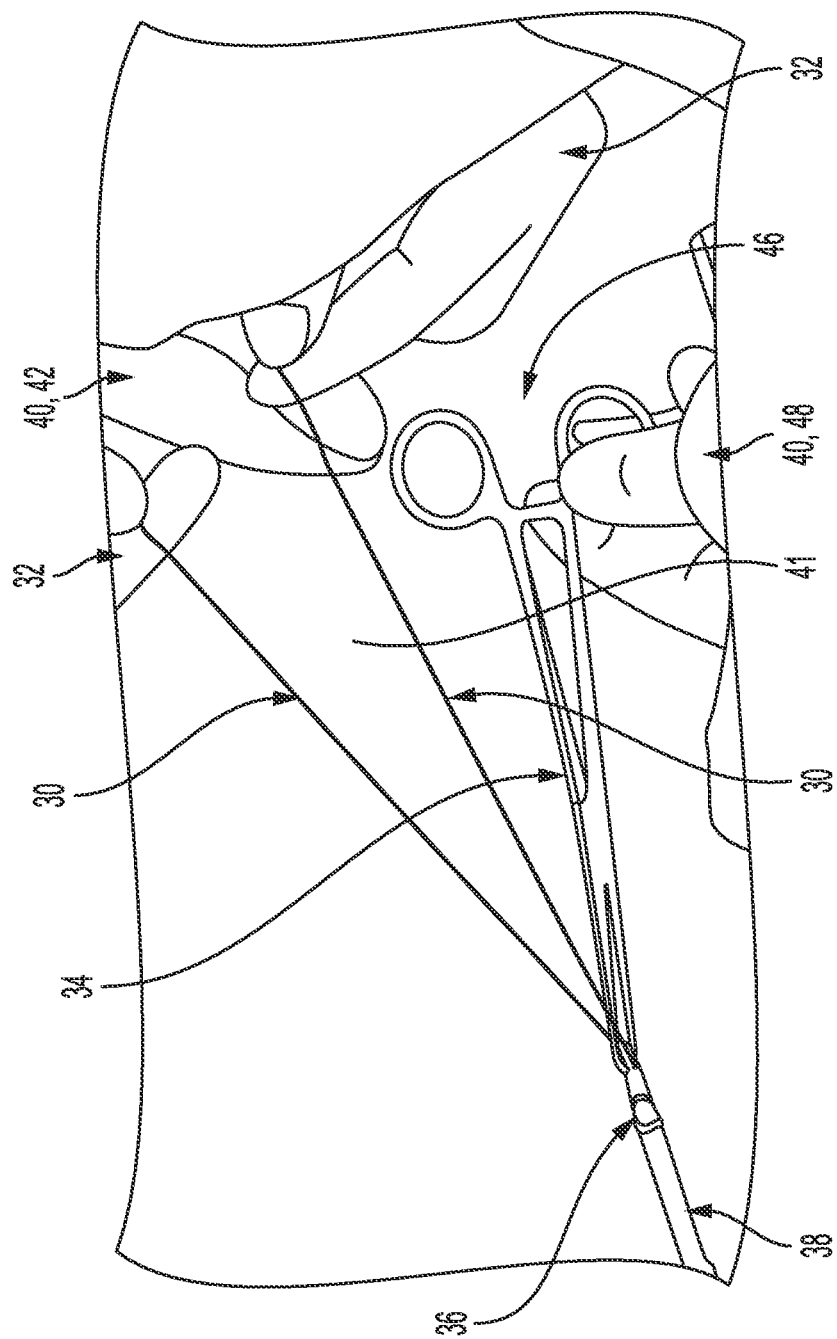
FIG. 5 is an isometric view of the prior art looped rope of FIG. 4, illustrating the second step of the example of the prior art labor intensive process for the use of the loop-based suturing method.
Figure 6:
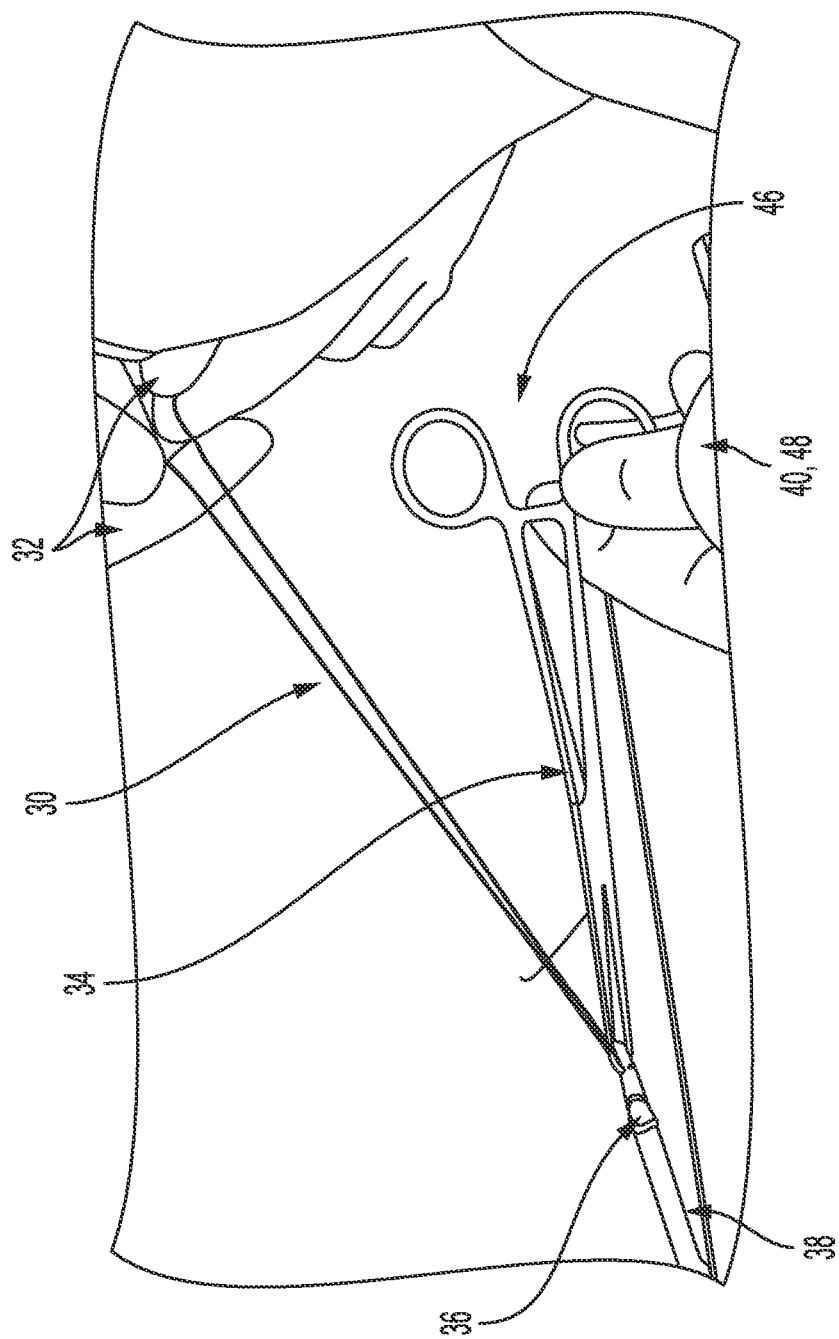
FIG. 6 is an isometric view of the prior art looped rope of FIG. 4, illustrating the third step of the example of the prior art labor intensive process for the use of the loop-based suturing method.
Figure 7:
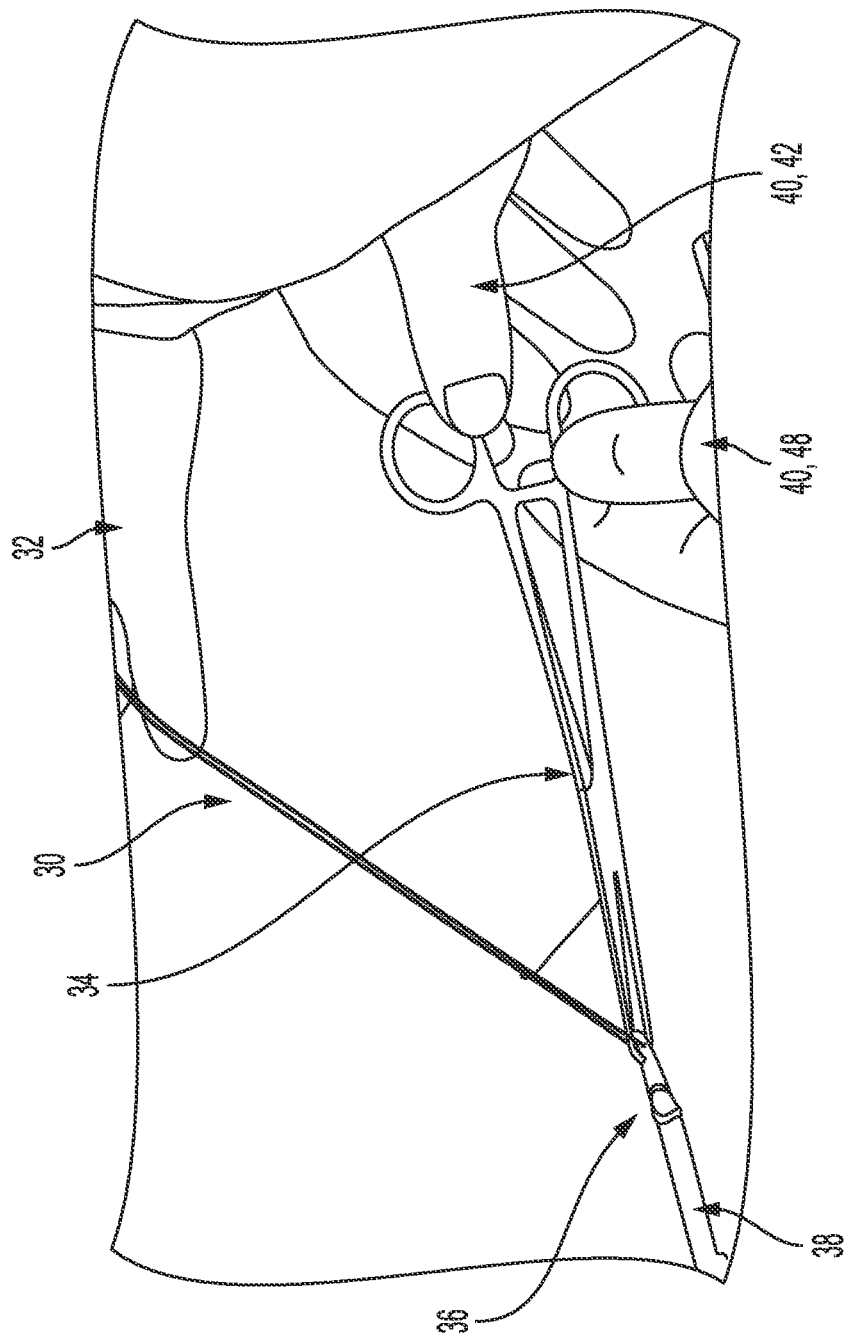
FIG. 7 is an isometric view of the prior art looped rope of FIG. 4, illustrating the fourth step of the example of the prior art labor intensive process for the use of the loop-based suturing method.
Figure 8:
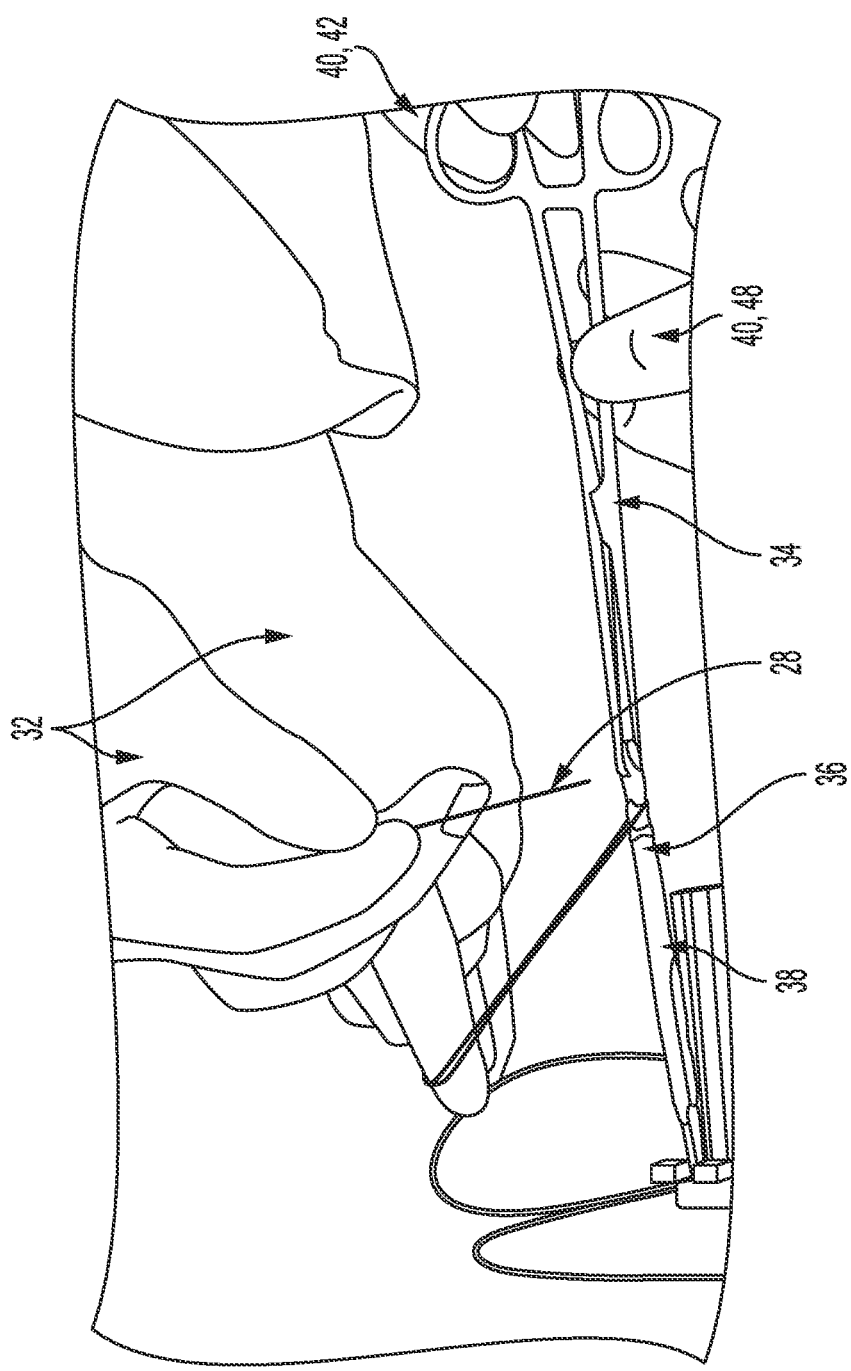
FIG. 8 is an isometric view of the prior art looped rope of FIG. 4, illustrating the fifth step of the example of the prior art labor intensive process for the use of the loop-based suturing method.
Figure 9:
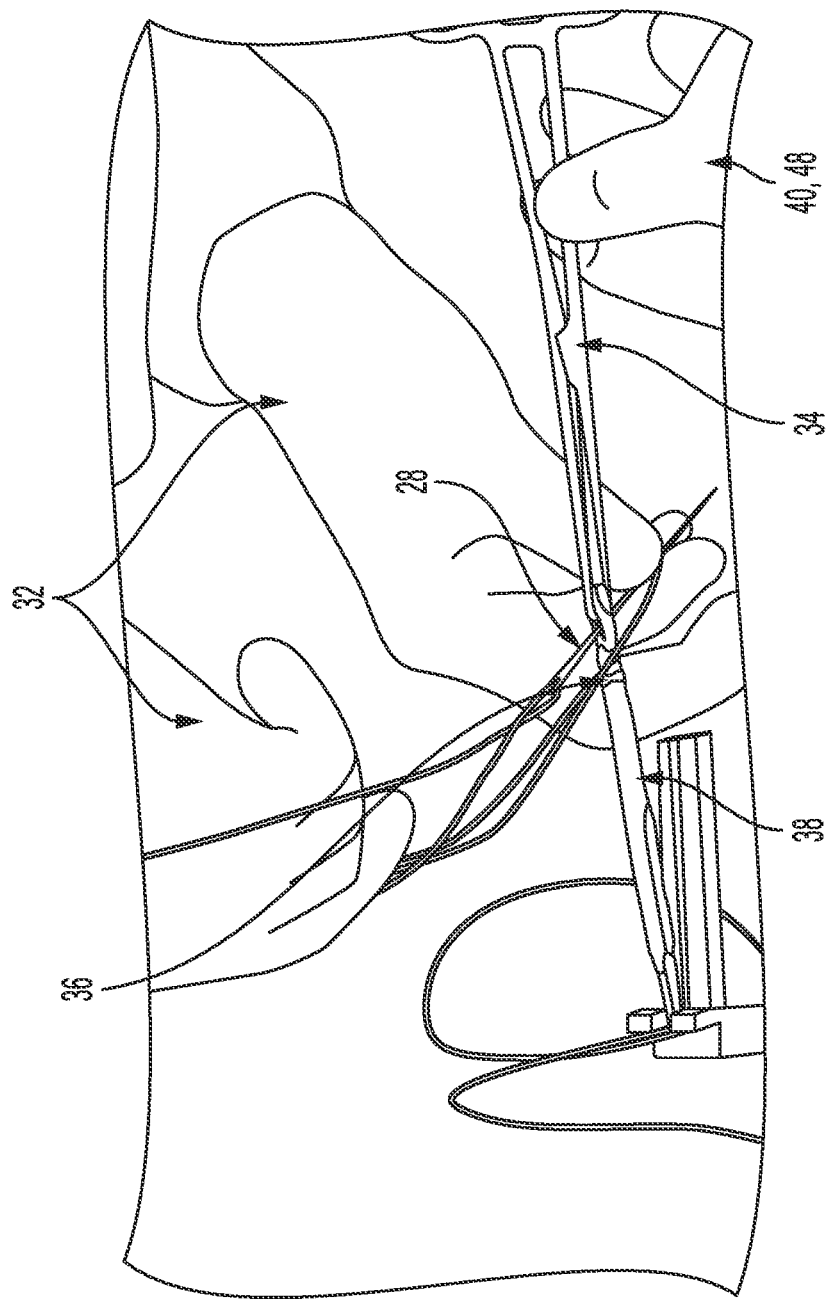
FIG. 9 is an isometric view of the prior art looped rope of FIG. 4, illustrating the sixth step of the example of the prior art labor intensive process for the use of the loop-based suturing method.
Figure 10:
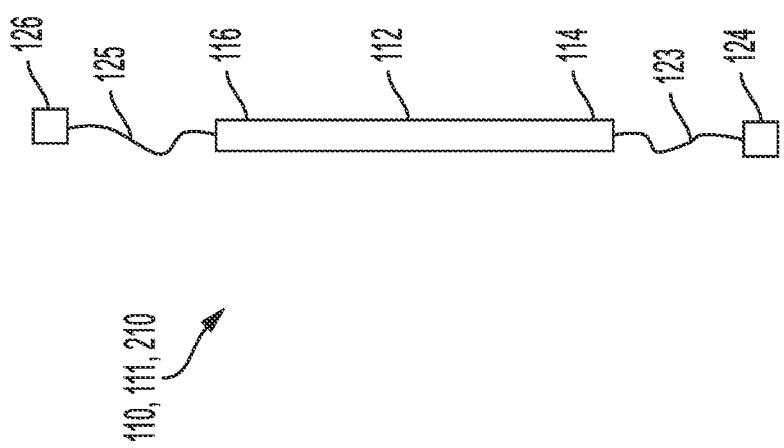
FIG. 10 is a top view of an embodiment of an implantable element.

Referring to FIG. 10, an implantable element 110 can include a graft of biological tissue excised from a patient or a graft of biological tissue supplied by a donor. For example, the implantable element 110 can include a portion of a tendon or a portion of a ligament. It should be understood, however, that the implantable element 110 can include any item suitable to be implanted or otherwise surgically coupled to a subject, such as a human or other animal undergoing medical treatment. Depending on the embodiment, the implantable element 110 can be natural or artificial, constructed of biological tissue (soft or hard) or constructed of a synthetic or non-biological material, such as a natural or synthetic rubber or any other suitable polymer, whether elastic, pierceable, flexible, pliable, deformable, semi-rigid or rigid.

Figure 11:
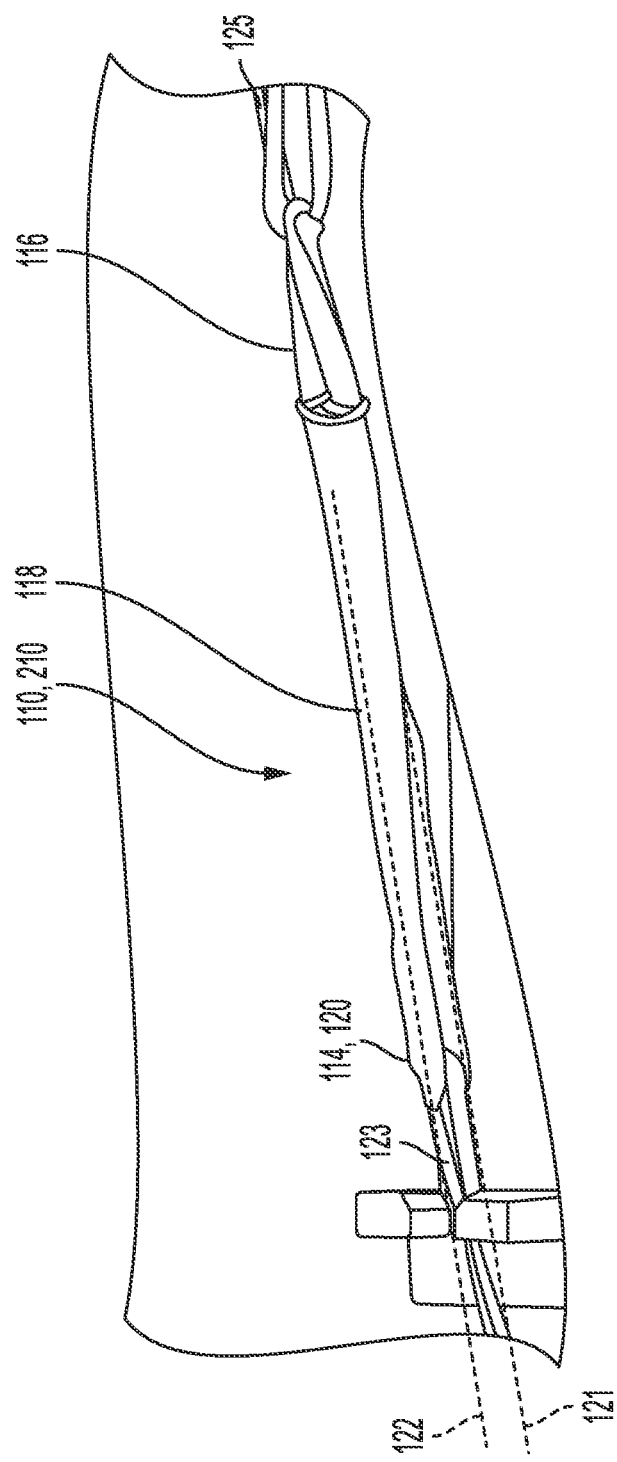
FIG. 11 is an isometric view of another embodiment of an implantable element.

In an embodiment, the implantable element 110 is a single-plane, implantable element 111 having: (a) an elongated body 112 extending along a single plane, which extends along a single longitudinal axis; (b) a first element end 114; and (c) a second element end 116. Alternatively, as illustrated in FIG. 11, the implantable element 110 can be a multi-plane, implantable element 210 having a body 118 that includes a single strip folded onto itself, forming a fold 120. Body 118 extends along multiple planes, which, in turn, extend along a plurality of longitudinal axes 121, 122.

A surgeon or other clinician can use a preoperative, pass-through preparation method to prepare the implantable element 110 to be secured to the surgical site of the subject. In an embodiment, the pass-through preparation method involves a loop-based suturing method, including, but not limited to, the FiberLoop® and TigerLoop® suturing methods published by Arthrex, Inc.

As illustrated in FIGS. 10-11, the pass-through preparation method for the implantable element 110 involves securing a plurality of harnesses, threads, ropes, cables or cords 123, 125 to the first and second element ends 114, 116, respectively. Depending on the type of surgery, the surgeon can install fasteners 124, 126 (e.g., medical screws or pins) to secure the cords 123, 125 to the subject's bone or otherwise within the surgical site.

Figure 12:
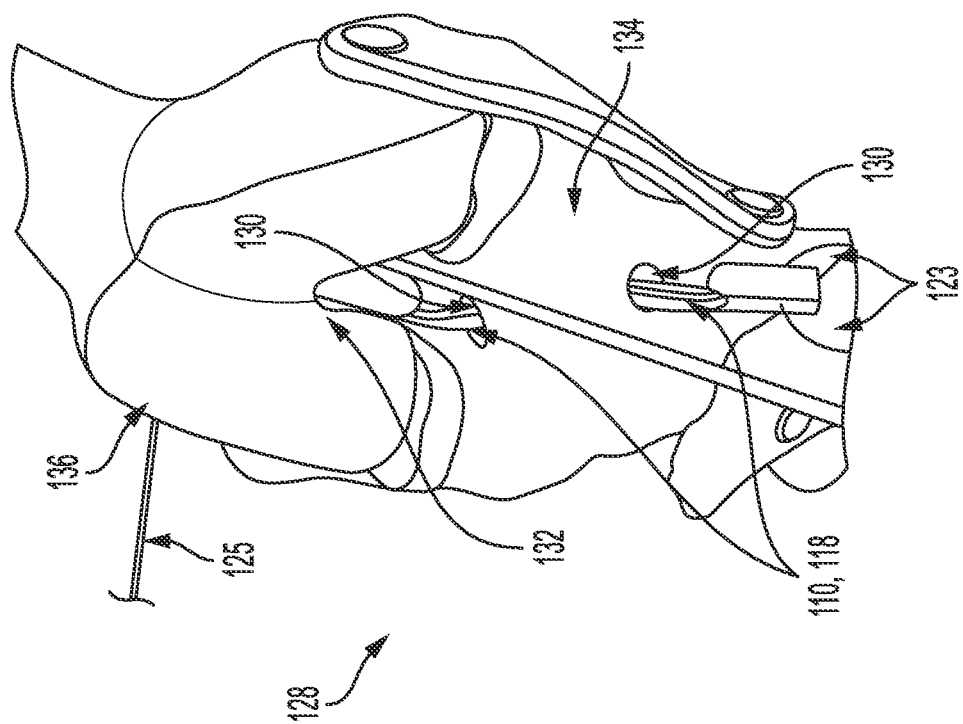
FIG. 12 is an isometric view of a knee site, illustrating an example of the implanting of an implantable element into the knee site.
Figure 13:
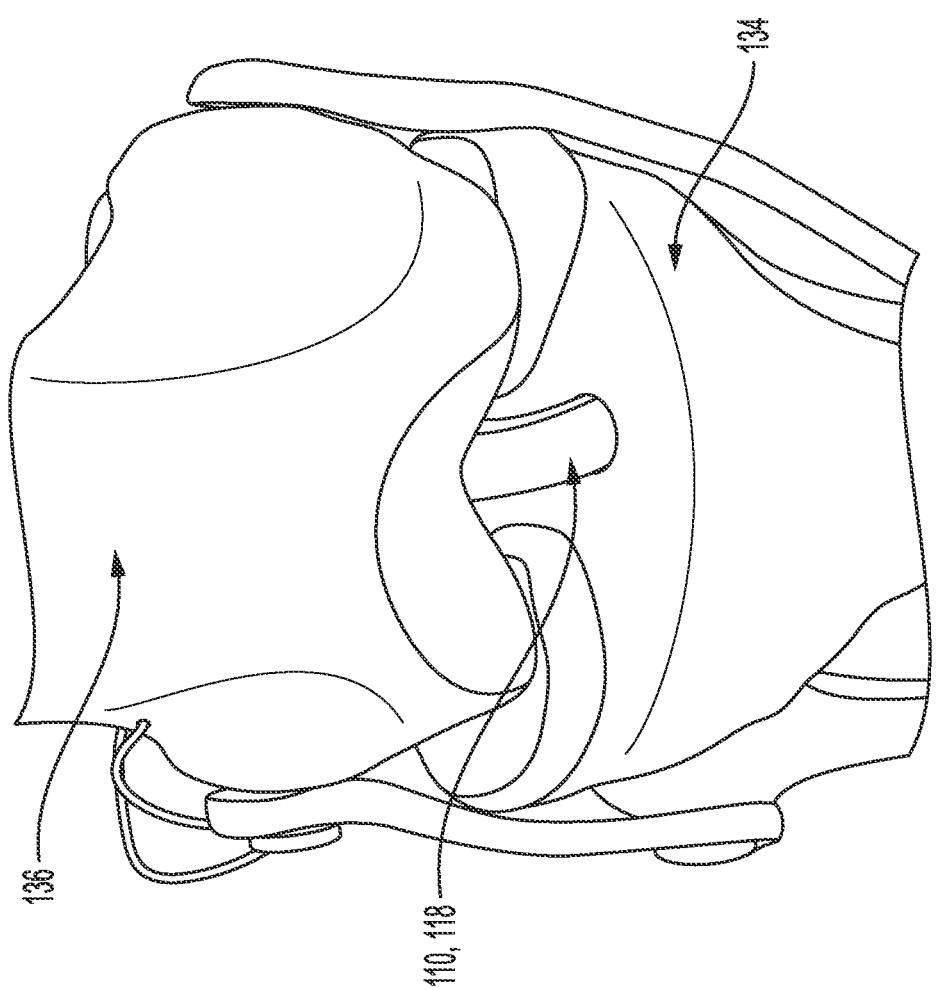
FIG. 13 is an enlarged isometric view of the knee site of FIG. 12, illustrating the implanting of the implantable element into the knee site.

In the example shown in FIG. 12, the implantable element 110 includes a tendon portion that has been prepared for ligament reconstruction within the knee site 128 of a subject. In this example, the subject's anterior cruciate ligament ("ACL") has been torn through injury and surgically removed. First, the surgeon secures the cords 123, 125 to the implantable element 110 according to the pass-through preparation method described below. Next, for the ACL reconstruction surgery, the surgeon drills tunnels 130, 132 in the subject's tibia 134 and femur 136, respectively. Then, the surgeon inserts the implantable element 110 into the tunnels 130, 132. After inserted and properly placed and tensioned, the surgeon binds the cords 125, 123 to tunnels 130, 132 by screwing fasteners (not shown) into the interior surfaces of the tunnels 130, 132. This results in the reconstructed ACL, as shown in FIG. 13.

Figure 14:
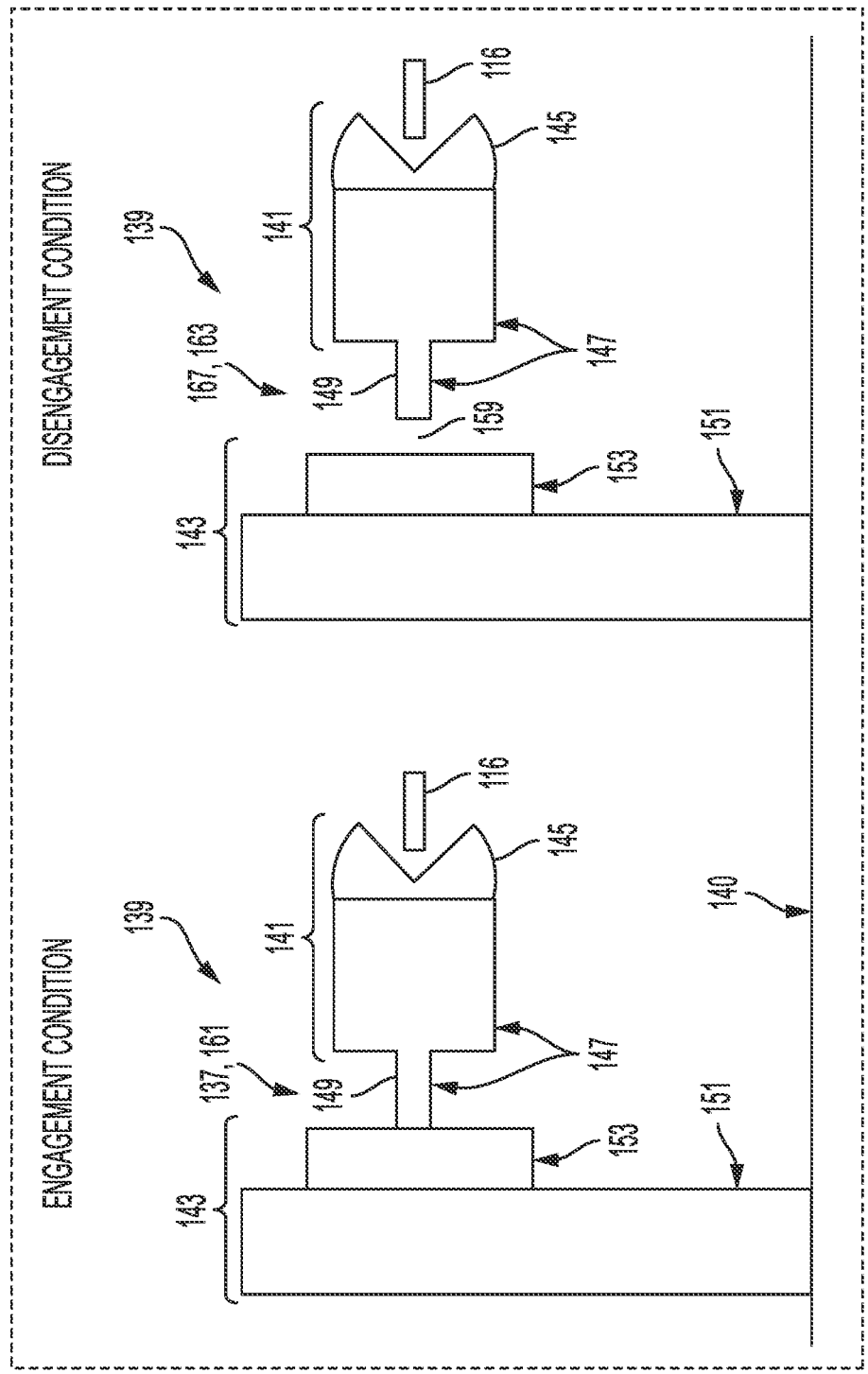
FIG. 14 is a schematic diagram of an embodiment of a medical holding system, illustrating the transition of the coupler portion from an engagement condition to a disengagement position.
Figure 15:
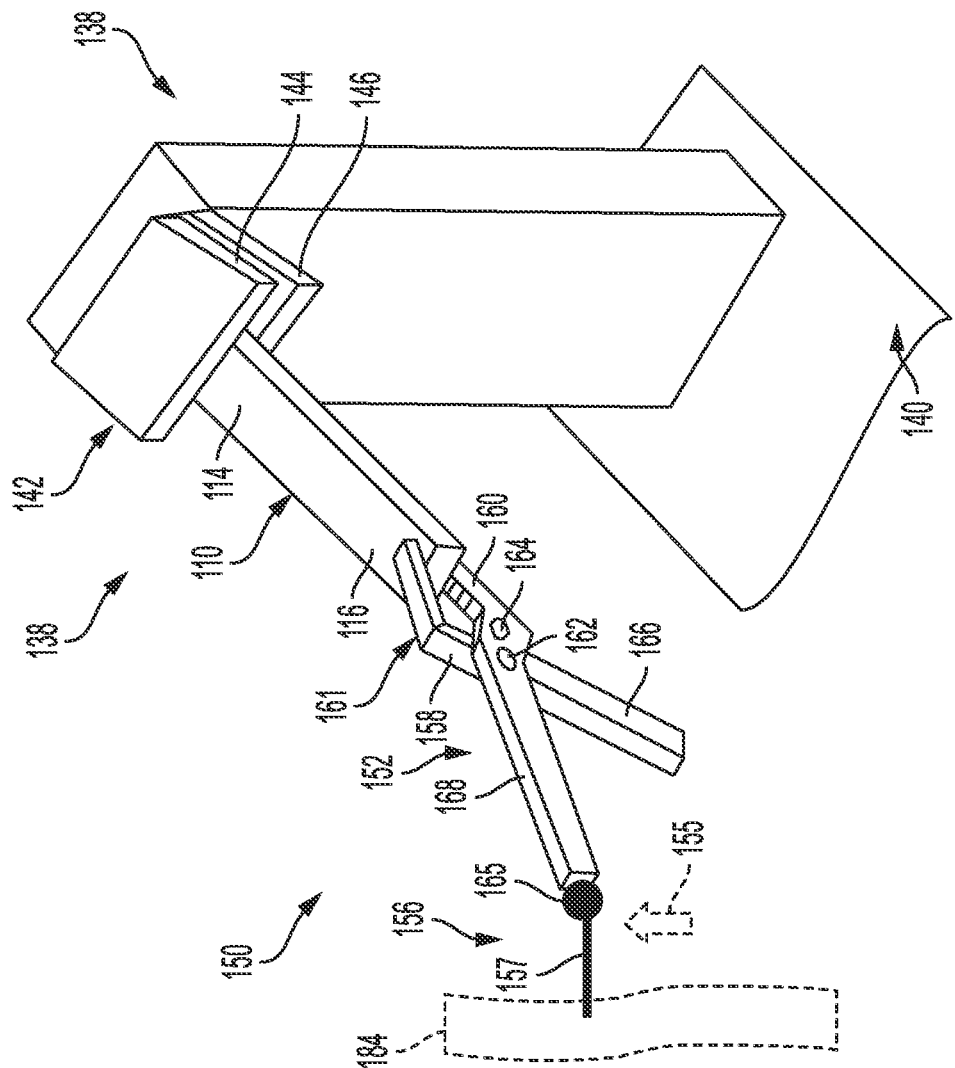
FIG. 15 is an isometric view of an embodiment of a medical holding system, illustrating the system's grasping of the end of an implantable element.

Referring to FIGS. 14-15, in an embodiment, the pass-through preparation method includes or incorporates the steps of a loop-based suturing method. This pass-through preparation method can be conducted by a single user, such as a single surgeon. To setup for this pass-through preparation method, the user uses a mount or hanger 138 (FIG. 15) to suspend the first element end 114 of the implantable element 110 above a support surface 140. In the embodiment shown in FIG. 15, the hanger 138 is an upright having a coupler configured to clamp or otherwise compress the first element end 114. To generate compression force on the first element end 114, the coupler 142 can sandwich the first element end 114 between a plurality of clamping members 144, 146, at least one of which is configured to move relative to the other. In an embodiment, the coupler 142 includes a fastener, such as a screw having a knob, that passes through threaded portions of the clamping members 144, 146. By rotating such fastener, the user can clamp or unclamp the first element end 114. It should be appreciated that any device or mechanism can be used to support, hang or suspend the first element end 114, including, but not limited to, a hook device, a holder or a clamping mechanism having one or more springs generating a predisposed clamping effect, pivot members, bolts, screws, pins or other fasteners.

Next, the user uses the medical holding assembly or medical holding system 139 (FIG. 14) or 150 (FIG. 15) to hold the second element end 116 while implementing the pass-through preparation method. The second element end 116 can be a free end or a medically-treatable end to be medically prepared or treated.

As illustrated in FIG. 14, in an embodiment, the medical holding system 139 includes: (a) a holder 141 configured to grasp or hold the second element end 116; and (b) a support device 143 configured to cooperate with the holder 141 to suspend the second element end 116 above the support surface 140. The holder 141 includes a grasper 145 configured to grasp and secure the second element end 116. The holder 141 also includes a coupler 147. The coupler 147 includes at least one coupler portion 149 configured to be reversibly coupled to the support device 143. The support device 143 includes an upright support 151 and a release interface 153 coupled to the upright support 151.

The holder 141 and the support device 143 are structured or configured to cooperate with each other so that the coupler portion 149 is configured to reversibly engage with the release interface 153. The cooperation between the holder 141 and the support device 143 can be mechanical, magnetic, electromechanical, electromagnetic or any other suitable form of cooperation.

The coupler portion 149 and the release interface 153 are configured to cooperate with each other so that coupler portion 149 is configured to be transitioned from an engagement condition 137 to a disengagement condition 167 and back to the engagement condition 137. In the engagement condition 137, the coupler portion 149 is engaged with the release interface 153 to keep the implantable element 110 suspended above the support surface 140 when the implantable element 110 is subject to a suturing force that acts downward toward the support surface 140. In the disengagement condition 167, the coupler portion 149 is temporarily disengaged from the release interface 153 in response to a pass-through force, thereby forming a passageway 159 between the support device 143 and the second element end 116. The passageway 159 is configured to receive a cord segment of a medical looped cord, as described below. After the cord segment passes through the passageway 159, the coupler portion 149 is configured or predisposed to transition back to the engagement condition 137. The coupler portion 149 and the release interface 153 are configured to keep the implantable element 110 suspended above the support surface 140 throughout the engagement and disengagement conditions 137, 167.

In an embodiment, the coupler portion 149 is configured to move between closed and open positions 161, 163 relative to the support device 143. In the closed position 161, the coupler portion 149 is engaged and in physical contact with the release interface 153, causing the passageway 159 to be closed. In the open position 163, the coupler portion 149 is disengaged and physically removed from the release interface 153, causing the passageway 159 to be temporarily opened.

In an embodiment, the pass-through force is an upward user force provided by the user. For example, the user can push or tap the coupler 147 or coupler portion 149 by using the user's finger, a taut segment of the looped cord, or the suturing needle. The coupler portion 147 and the release interface 153 are configured to keep the implantable element 110 suspended above the support surface 140 throughout the engagement and disengagement conditions 137, 167 without relying or depending on the continuation of such upward user force or any other user force. In a series of repeated transitions between the engagement and disengagement conditions 137, 167, the passageway 159 repeatedly transitions between closed and open. Each opening of the passageway 159 enables the user to pass the medical cord between the support device 143 and the second element end 116 while keeping the implantable element 110 from falling to the support surface 140.

In the embodiment illustrated in FIG. 15, the medical holding system 150 includes: (a) a holder 152 configured to hold the second element end 116; and (b) a support device 154 (FIG. 21) configured to cooperate with the holder 152 to suspend the second element end 116 above the support surface 140. To best illustrate the operation of the pass-through preparation method in this embodiment, the support device 154 is omitted from FIGS. 15-20. It should be understood that the support device 154 (FIGS. 21-23) generates an upward support force 155 during the pass-through preparation method. Depending on the embodiment, the support force 155 can vary during the pass-through preparation method.

As shown in FIG. 15, the user secures the holder 152 to the second element end 116. In an embodiment, the holder 152 includes: (a) a grasper 161 configured to be attached to the second element end 116; and (b) a coupler 156 connected to and extending from the grasper 161. In an embodiment, the grasper 161 includes: (a) a plurality of jaws 158, 160 moveable relative to each other; (b) a pivot member 162 configured to pivotally couple the jaws 158, 160 together; (c) a position lock 164 configured to lock or secure the jaws 158, 160 in a desired, fixed position relative to each other; and (d) a plurality of handles or extensions 166, 168 extending from the jaws 158, 160, respectively. In such embodiment, the coupler 156 extends from one or both of the extensions 166, 168. As described below, in an embodiment, the coupler 156 includes a support engager or coupler portion 157 coupled to a connector 165. Depending on the embodiment, the connector 165 can include a joint (e.g., a ball joint or other type of joint), hinge, rotary or pivot member.

Figure 16:
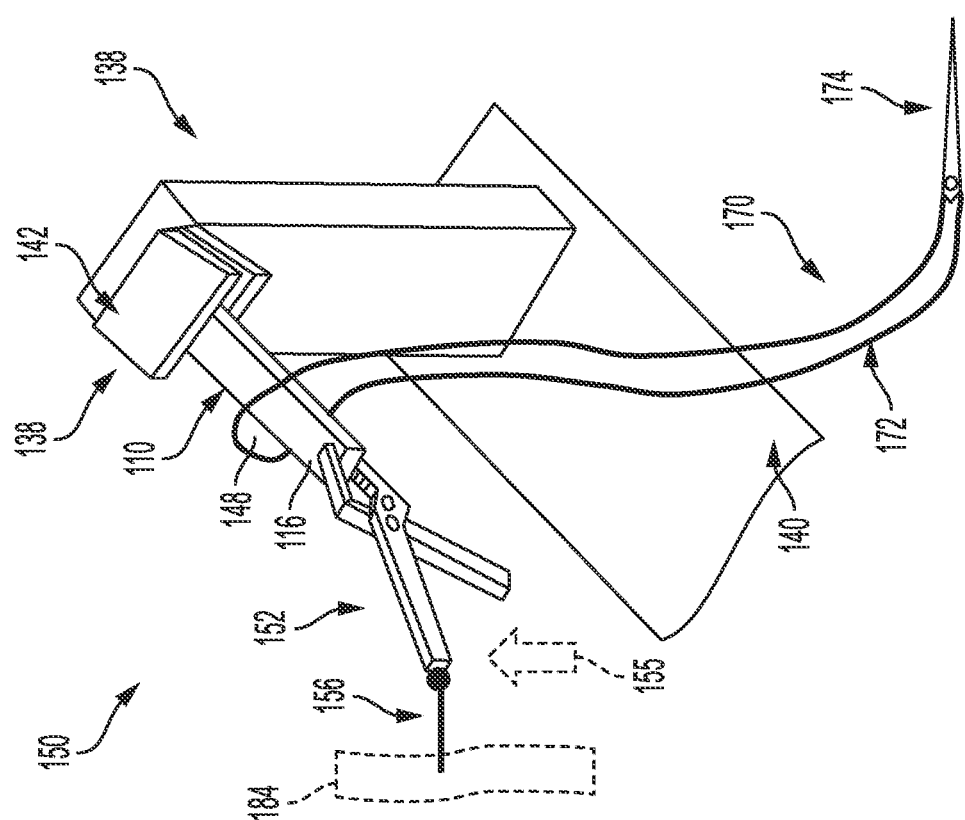
FIG. 16 is an isometric view of the medical holding system of FIG. 15, illustrating a looped cord that is looped around the end of the implantable element.

Referring to FIG. 16, before or after the user secures the holder 152 to the second element end 116, the user inserts the second element end 116 through the loop opening 148 defined by a cord assembly 170. In an embodiment, the cord assembly 170 includes a looped cord 172 and a piercer or needle 174. Depending on the embodiment, the looped cord 172 can include a ring, hoop or loop of any rope, thread, wire, belt, cable or other cord. The looped cord 172 can be constructed of any suitable, flexible material, including, but not limited to, polymer, natural or synthetic fibers, natural or synthetic rubber, or flexible metal.

The assembly process for the cord assembly 170 begins with a single cord having two free ends. The assembler passes one of the free ends through the eye of the needle 174. Next, the assembler mechanically bonds, fuses, ties or otherwise connects such free end to the other free end of the cord to form the looped cord 172. The needle 174 is free to slidably engage with the looped cord 172.

Figure 17:
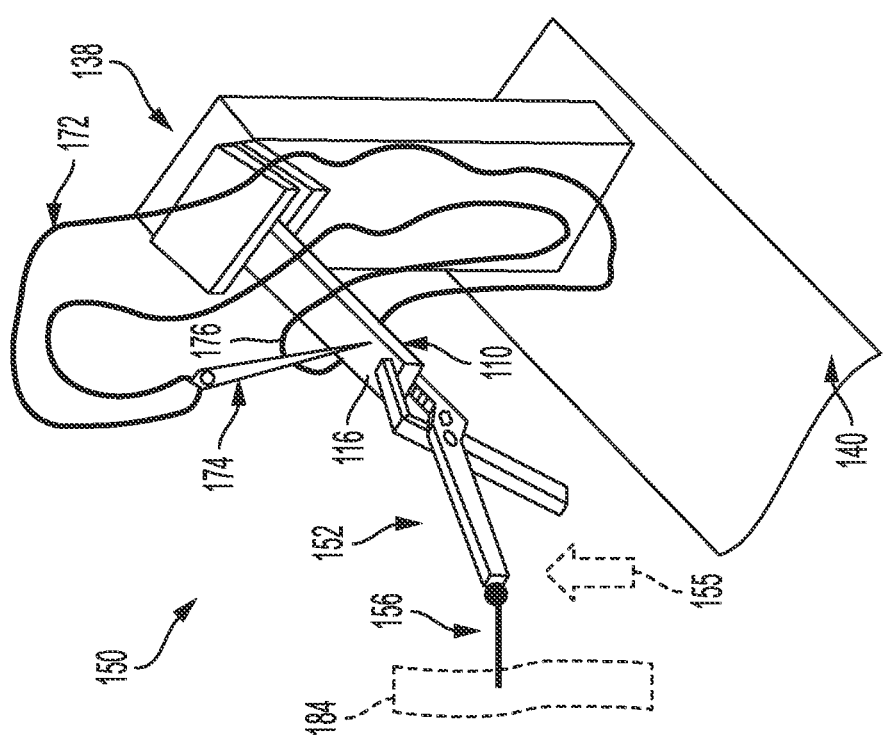
FIG. 17 is an isometric view of the medical holding system of FIG. 15, illustrating the first piercing of the end of the implantable element at a location in front of the loop.
Figure 18:
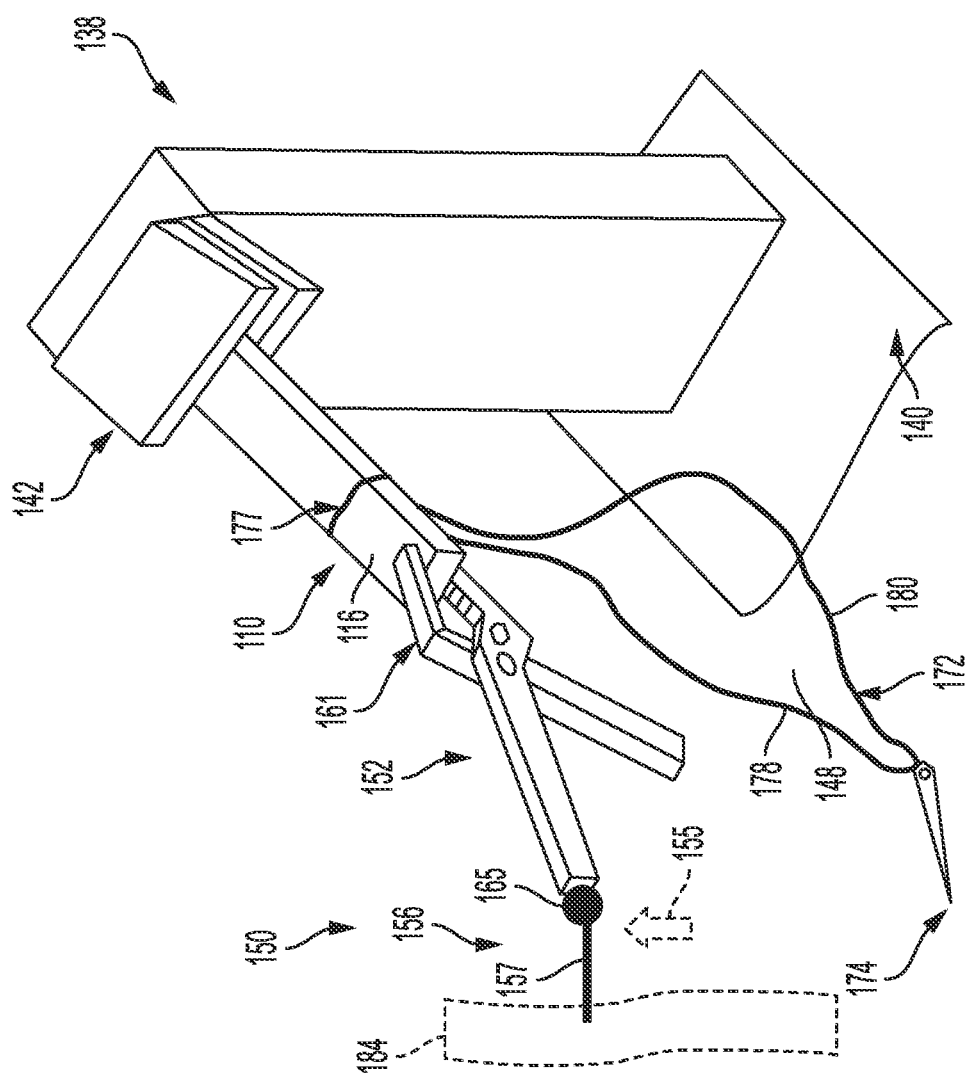
FIG. 18 is an isometric view of the medical holding system of FIG. 15, illustrating the first suture line resulting from the first piercing step.
Figure 19:
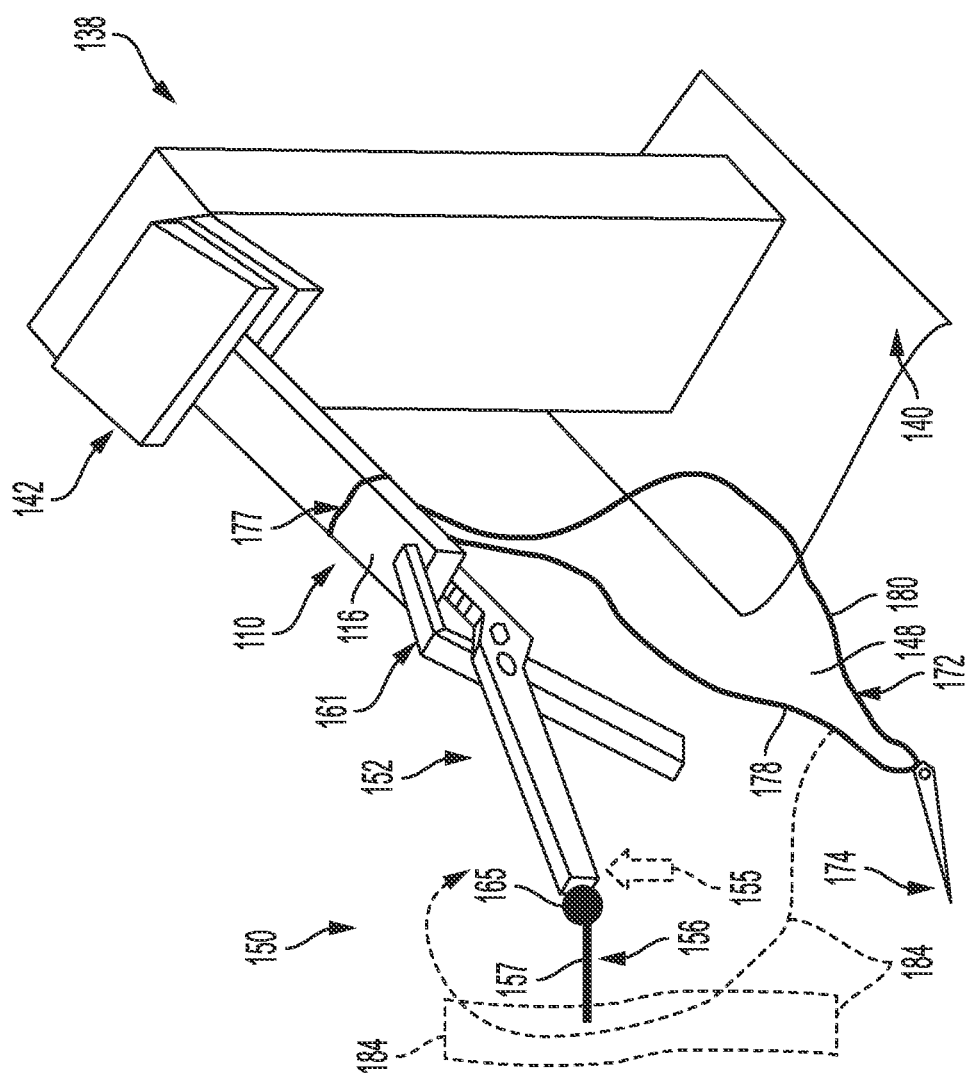
FIG. 19 is an isometric view of the medical holding system of FIG. 15, illustrating the formation of a passageway that receives a segment of the cord to enable a pass-through of the cord segment.
Figure 20:
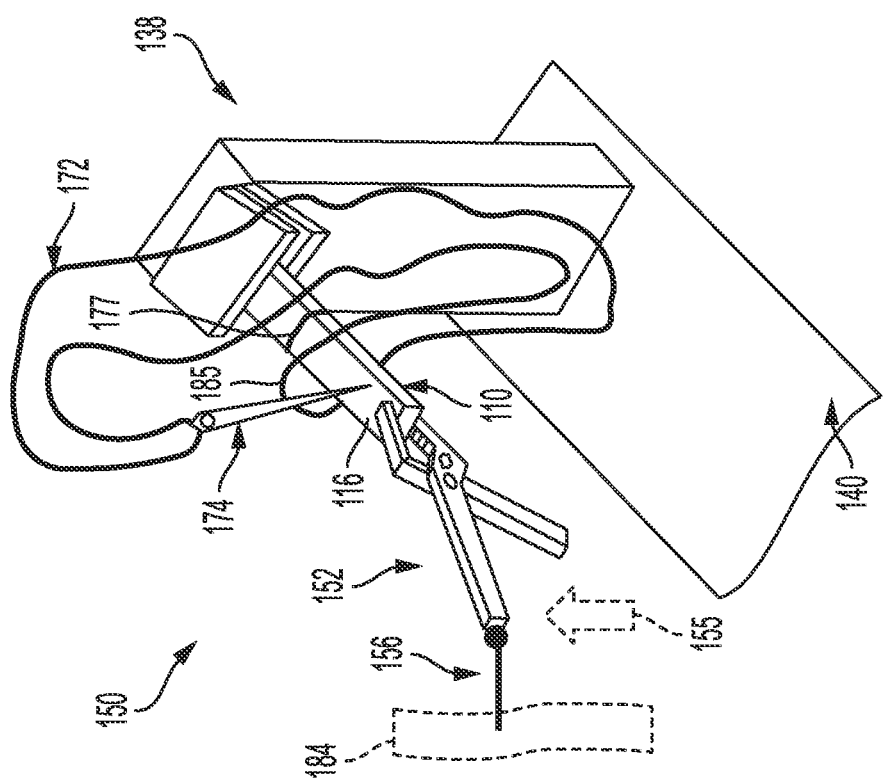
FIG. 20 is an isometric view of the medical holding system of FIG. 15, illustrating the second piercing of the end of the implantable element at a location in front of the first suture line.

Referring to FIG. 17, next, the user pierces the second element end 116 and passes the needle 174 entirely through the second element end 116. As shown, the piercing occurs in front of the loop section 176. This results in an initial suture line 177, as shown in FIG. 18. As illustrated in FIGS. 18-19, the user next spreads the loop segments 178, 180 apart to form the loop opening 148. The user moves the loop segment 178 upward through the passageway 184 while passing the holder 152 through the loop opening 148. Next, as illustrated in FIG. 20, the user forms another loop section 185 around the second element end 116, and the user pierces the second element end 116 and passes the needle 174 entirely through the second element end 116. As part of the pass-through preparation method, the user repeats the steps illustrated in FIGS. 17-20 until establishing a desired number of suture lines in the second element end 116. This results in a looped cord 172 that is firmly secured to the second element end 116. The user may cut the looped cord 172, remove the needle 174, and use the two segments of the cut looped cord 172 to secure the implantable element 110 within a surgical site as described above. It should be appreciated that the user can perform the same pass-through preparation method on the first element end 114.

Figure 21:
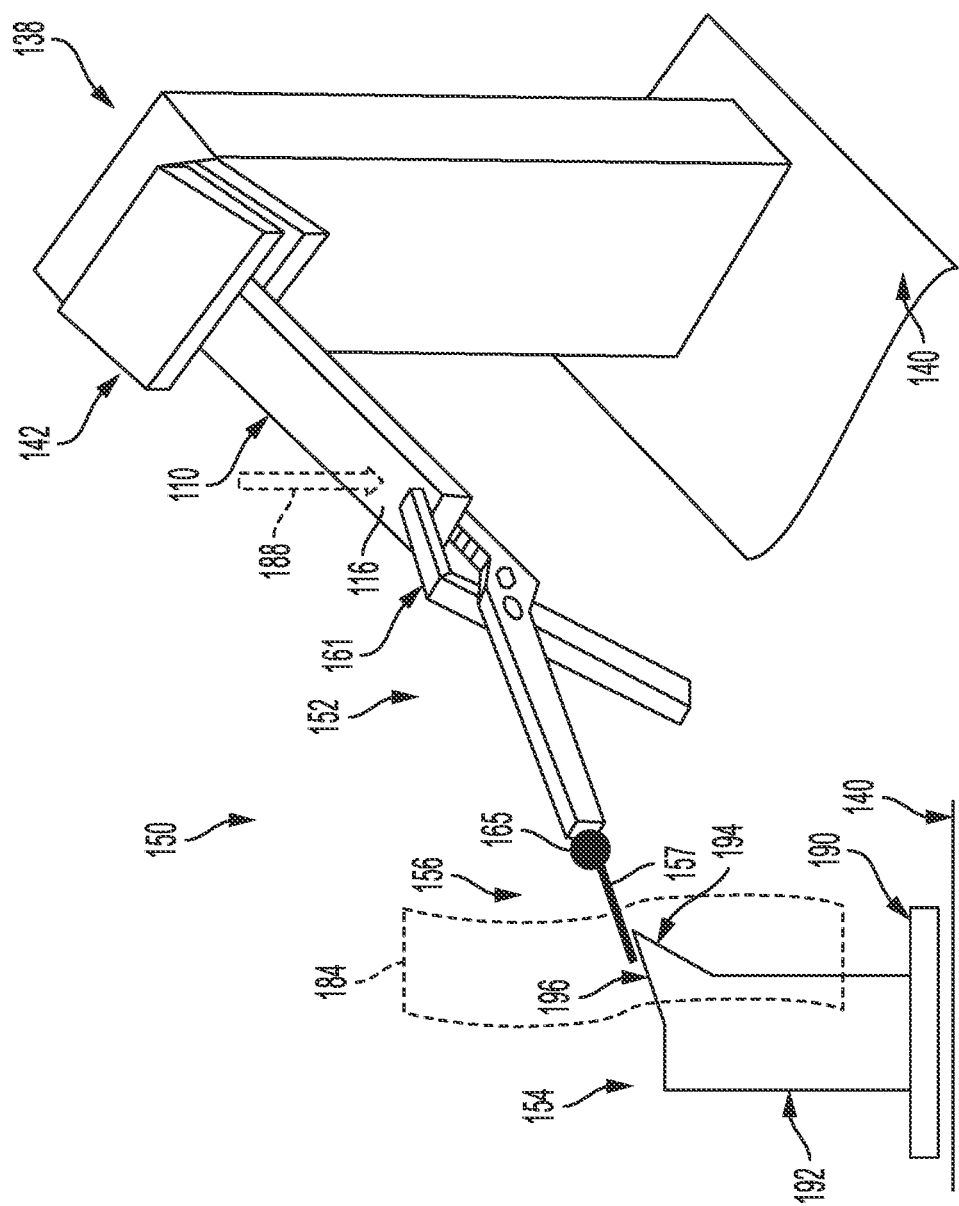
FIG. 21 is an isometric view of the medical holding system of FIG. 15, illustrating the cooperation between the coupler and the support device when the coupler portion is in a closed position.
Figure 22:
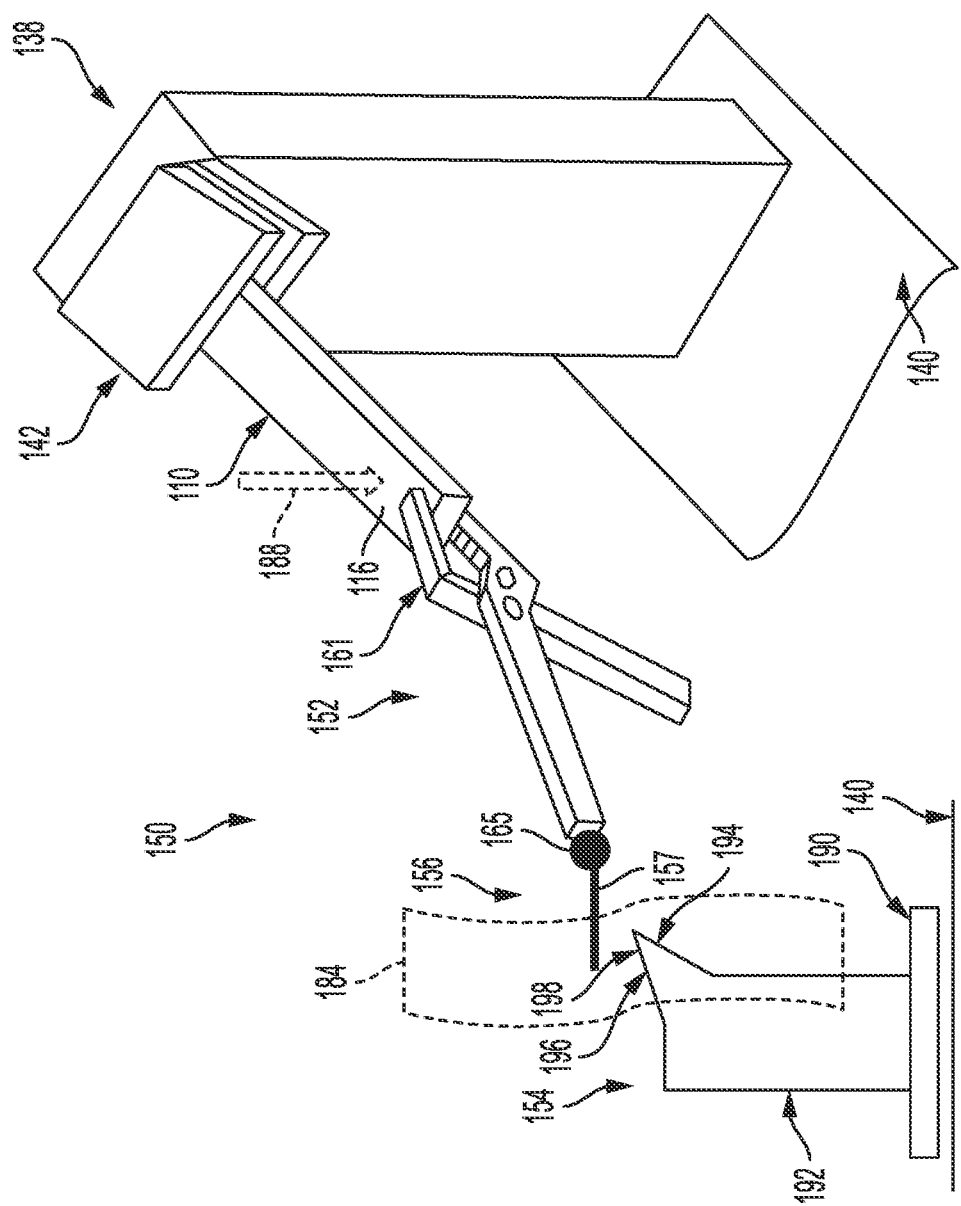
FIG. 22 is an isometric view of the medical holding system of FIG. 15, illustrating the cooperation between the coupler and the support device when the coupler portion is in an open position.

As illustrated in FIGS. 21-22, the support device 154 of the medical holding system 150 generates the upward support force 155 described above. Accordingly, the support device 154 prevents the second element end 116 from falling or dropping to the support surface 140 during the pass-through preparation method. In other words, the support device 154, in cooperation with the hanger 138, keeps the implantable element 110 suspended despite the downward piercing force 188.

In an embodiment, the support device 154 includes: (a) a base 190 defining one or more holes (not shown) configured to receive one or more fasteners (not shown) to removably mount the base 190 to the support surface 140; (b) an upright portion or support body 192 extending upward from the base 190; and (c) a support member 194 coupled to, extending from, or otherwise supported by the support body 192.

The support member 194, in an embodiment, includes a release interface 196 and a stopper 198. In an embodiment, the release interface 196 is the surface portion of the support member 194 that is positioned to make physical contact with the coupler portion 157 of the coupler 156. In an embodiment, the stopper 198 is a portion of the release interface 196 that is configured to stop or prevent the coupler portion 157 from falling to the support surface 140. In the embodiment shown in FIGS. 21-22, the release interface 196 is the same as the stopper 198. In another embodiment, the release interface 196 includes any structure, material or characteristic configured to urge the coupler portion 157 into reversible engagement with the support member 194.

For example, in an embodiment, the release interface 196 and the coupler portion 157 are structured or configured to be magnetically attracted to each other. In an embodiment, the release interface 196 includes a magnetic characteristic operable to magnetically attract the coupler portion 157 to the support member 194. In such embodiment, the coupler portion 157 and the release interface 196 include a suitable combination of metallic or magnetic characteristics. One or each of the coupler portion 157 and the release interface 196 can include a magnet or a magnetizable element configured to be magnetized, including, but not limited to, an electromagnet. In the case of an electromagnet, the medical holding system 150 includes: (a) a coil of wire surrounding a core of ferromagnetic material, such as steel; (b) an electrical circuit operatively coupled to the coil; and (c) an electrical power cord or battery power source operatively coupled to the electrical circuit.

In an embodiment, the medical holding system 150 includes a magnetic shield configured and arranged to block any level of undesirable amount of magnetic fields generated by the coil of wire, electromagnet, magnets or other magnetic field generators of the medical holding system 150. The magnetic shield can be constructed of: (a) sheet metal, metal screen, metal foam, copper, nickel and any other suitable conductive material; and (b) a grounding connector operable to electrically ground the magnetic field generator to the chassis or housing of the medical holding system 150, to the support surface 140, or otherwise to earth ground. Accordingly, the magnetic shield can reduce risks of the medical holding system 150 creating electrical interference with electrical hospital equipment or electrical medical devices implanted in subjects.

Figure 23:
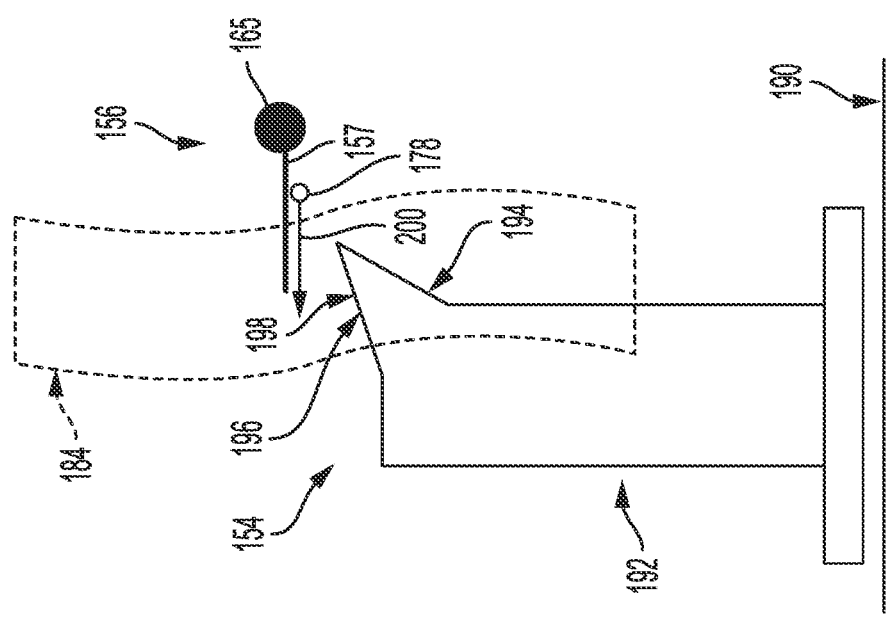
FIG. 23 is an enlarged, side elevation view of the medical holding system of FIG. 15, illustrating the coupler portion in the open position.

With continued reference to FIGS. 21-23, the coupler portion 157 and the release interface 196 are configured to cooperate with each other so that the coupler portion 157 is predisposed to remain engaged with the release interface 196. During the engagement, the second element end 116 remains suspended above the support surface 140 when the implantable element 110 is subject to the downward piercing force 188. The predisposition of engagement can be due to gravity (a combination of the weight of the holder 152 and the weight of the implantable element 110) and the piercing force 188. Alternatively, as described above, the predisposition of engagement can be due to a magnetic attraction, spring-based mechanism or other phenomena.

When the user is ready to pass the loop segment 178 (FIG. 19) through the passageway 184, as described above, the user can apply an upward pass-through force to the coupler portion 157. In response, the coupler portion 157 disengages the release interface 196, thereby forming the passageway 184 between the support device 154 and the second element end 116. The passageway 184 is configured to receive the loop segment 178.

Referring to FIG. 23, the user can generate the upward, pass-through force in various ways and methods. For example, the user can stretch the loop segment 178 of the looped cord 172 so that the cord segment or loop segment 178 is relatively tight. Next, the user can drag the loop segment 178 in the rearward direction 200 until clearing the coupler portion 157 and reaching the passageway 184. Alternatively, the user can push the needle 174 (FIG. 19) upward against the coupler portion 157 until the needle 174 (and loop segment 178) reach the passageway 184. Also, the user can tap or press the user's finger upward against the coupler portion 157 while slipping the loop segment 178 beyond the coupler portion 157 until the loop segment 178 reaches the passageway 184. In either method, a single user can repeatedly and periodically move the loop segment 178 into the passageway 184 with relative ease and quickness.

Because the coupler portion 157 is predisposed to be engaged with the release interface 196, the coupler portion 157 re-engages the release interface 196 after the loop segment 178 passes into the passageway 184. In this way, the coupler portion 157 is operable as a gate configured to be periodically opened, providing temporary access to the passageway 184. Consequently, the implantable element 110 remains suspended above the support surface 154 while the user periodically passes the loop segment 178 through the passageway 184 during the pass-through preparation method.

In an embodiment, the medical holding system 150 enables a single user to conveniently perform the pass-through preparation method. Depending on the embodiment, the medical holding system 150 can produce a threshold level of tension in the implantable element 110 during the pass-through preparation method. This threshold level of tension can be equal to, substantially equal to, or correspond with, the indwelling tension that the surgeon will set for the implantable element 110 when implanting the implantable element 110 in the subject. Depending on the embodiment, the tension during the pass-through preparation method can decrease during the formation of the passageway 184, and the tension can then return to the threshold tension by the time the needle 174 pierces the implantable element 110. Accordingly, the construction of the stitching or suturing in the second element end 116 can provide strength that is sufficient to withstand the indwelling tension of the implantable element 110 when implanted in the subject.

Figure 24:
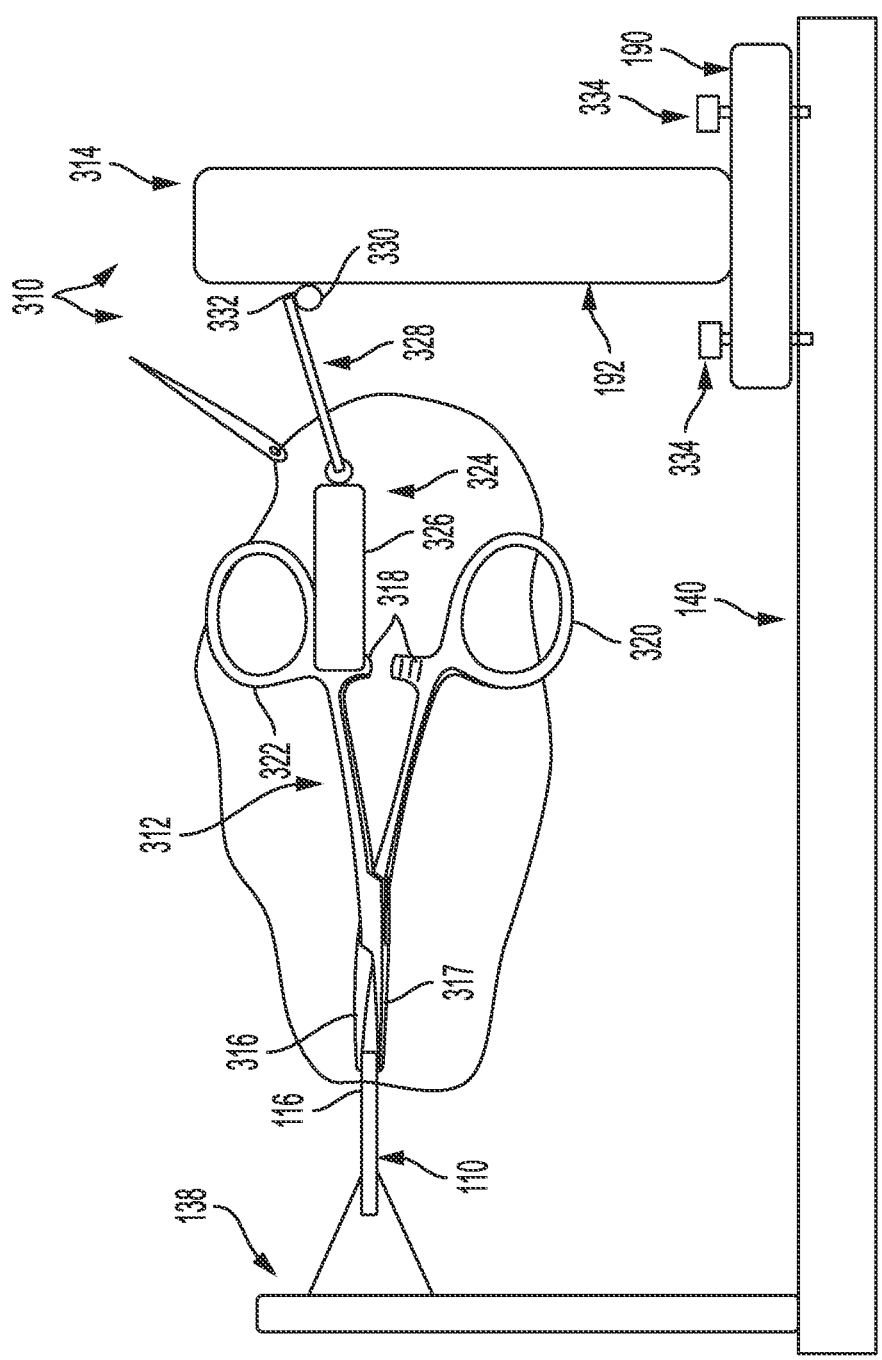
FIG. 24 is a side elevation view of another embodiment of a medical holding system, illustrating the coupler portion in a closed position.

In an embodiment illustrated in FIG. 24, the medical holding system 310 includes the same structure, parts, elements and functionality as medical holding system 150 except that the medical holding system 310 includes holder 312 and support device 314. Holder 312 includes: (a) a plurality of jaws 316, 317 pivotally coupled together; (b) a position lock 318 configured to reversibly lock the jaws 316, 317 in a desired position when the jaws 316 are clamped onto the second element end 116; (c) a plurality of handles 320, 322; and (d) a coupler 324 connected to the handle 322.

The coupler 324 includes a connector 326 attached to the handle 320, and a coupler portion 328 coupled to the connector 326. Depending on the embodiment, the connector 326 can include a joint (e.g., ball joint), hinge, rotary or pivot member.

Figure 25:
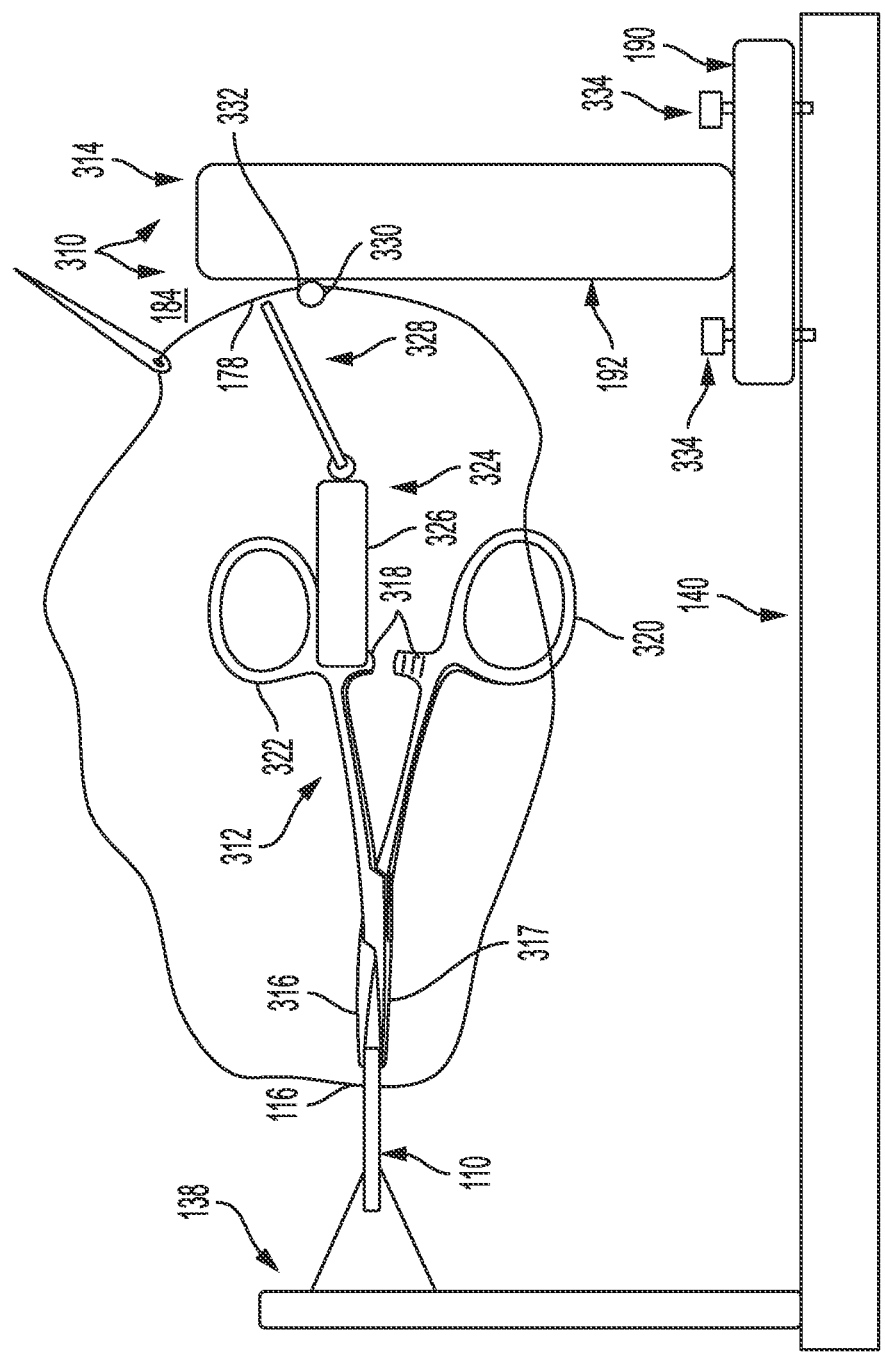
FIG. 25 is a side elevation view of the medical holding system of FIG. 24, illustrating the coupler portion in an open position.

The support device 314 includes: (a) a support member 330 having a release interface 332; and (b) a plurality of fasteners 334 configured to be inserted through the base 190 and screwed into the support surface 140. The release interface 332 is configured to be magnetically attracted to the coupler portion 328. As illustrated in FIG. 25, during the pass-through preparation method, the user periodically passes the cord segment or loop segment 178 of the looped cord 172 between the coupler portion 328 and the support member 330 until the loop segment 178 reaches the passageway 184. During the passage, the user generates an upward force on the coupler portion 328 that overcomes the magnetic force of attraction between the coupler portion 328 and the release interface 332. The periodic passages enable the user to conveniently perform the pass-through preparation method.

Figure 26:
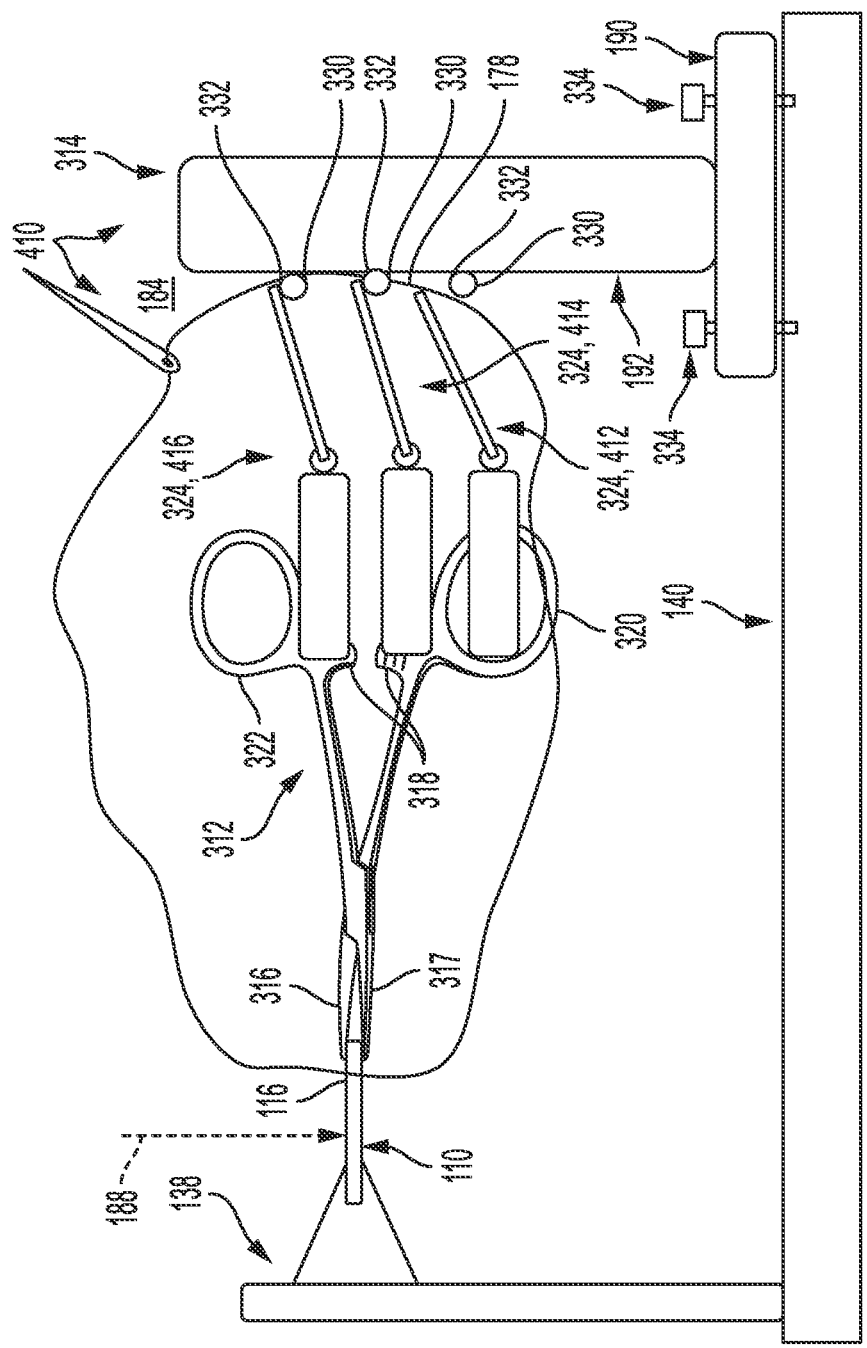
FIG. 26 is a side elevation view of yet another embodiment of a medical holding system, illustrating an example of a bottom coupler portion in an open position and two other coupler portions in closed positions.

In an embodiment illustrated in FIG. 26, the medical holding system 410 includes the same structure, parts, elements and functionality as medical holding system 310 except that the medical holding system 410 includes: (a) a plurality of couplers 324; and (b) a plurality of support members 330, each of which has a release interface 332. Based on this arrangement, the medical holding system 410 provides a series of gates 412, 414, 416 that are vertically stacked. In an embodiment, at all times during the pass-through preparation method, at least one of the gates 412, 414, 416 is closed, while one or more of the other gates 412, 414, 416 can be in an open position. This ensures that, at all times, the support device 314 is physically supporting the second element end 116.

In operation of one example, as illustrated in FIG. 26: (a) the user first passes the cord segment or loop segment 178 through gate 412; (b) then, gate 412 closes due to a magnetic force; (c) then, the user passes the loop segment 178 through gate 414; (d) then, gate 414 closes due to a magnetic force; and (e) then, the user passes the loop segment 178 through gate 416 to proceed with suturing the second element end 116. In this example, at all times during the pass-through preparation method, two of the gates 412, 414, 416 are closed. The number of gates in the medical holding system 410 can be adjusted based on the piercing force 188 necessary to pierce the applicable implantable element 110. For example, a relatively soft implantable element 110, suitable for a relatively low piercing force 188, can be sutured with the use of two gates, and a relatively hard implantable element 110, requiring a relatively high piercing force 188, can be sutured with the use of five gates.

Figure 27:
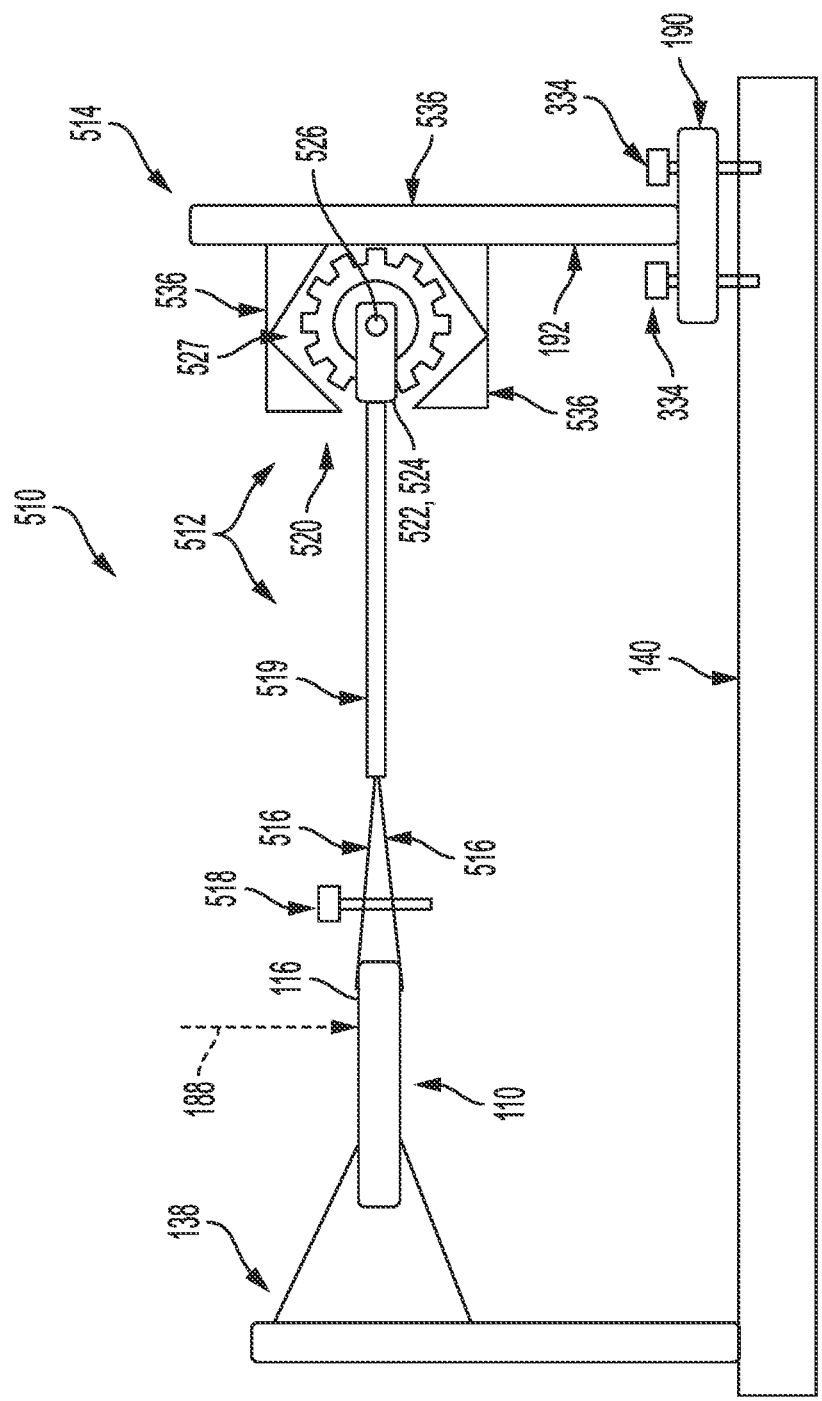
FIG. 27 is a side elevation view of still another embodiment of a medical holding system, illustrating the multiple coupler portions of a rotary coupler.
Figure 28:
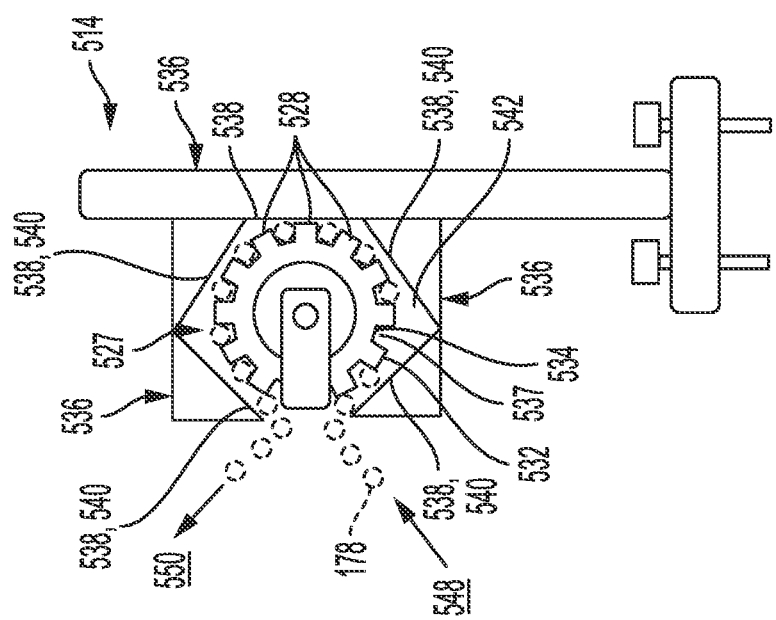
FIG. 28 is an enlarged side elevation view of the coupler of the medical holding system of FIG. 27, illustrating the coupler portions spaced apart by valley spaces.

In an embodiment illustrated in FIGS. 27-28, the medical holding system 510 includes the same structure, parts, elements and functionality as medical holding system 150 except that the medical holding system 510 includes holder 512 and support device 514. Holder 512 includes: (a) a plurality of jaws 516 configured to be clamped or squeezed onto the second element end 116; (b) a fastener 518 (e.g., a screw or bolt) configured to draw the jaws 516 together and secure the jaws 516 in a position that compresses the second element end 116; (c) a rigid extension or arm 519 extending from the jaws 516; (d) a coupler 520 attached to the arm 519.

Depending on the embodiment, the fastener 518 can include a screw having a grasp or knob to facilitate rotation by the user's hand. In this embodiment, the coupler 520 includes a connector 522 having a yoke or fork-shaped frame 524, and a shaft 526 coupled to the fork-shaped frame 524. The coupler 520 also includes a wheel, disk, gear or rotor 527 that is rotatable relative to the support device 514. In the embodiment shown, the rotor 527 is rotatably coupled to the shaft 526. The rotor 527 includes a plurality of coupler portions 528 that are spaced apart from each other. As shown in FIG. 28, each coupler portion 528 is a protrusion, tooth or projection extending from the rotor 527, providing the rotor 527 with a forming a gear configuration. In this embodiment, each coupler portion 528 has a peak surface 532. In between each coupler portion 528 is a valley surface 534. Depending on the embodiment, the rotor 527 can have a compliant, flexible or deformable surface or characteristic. For example, the coupler portions 528, peak surfaces 532 and valley surfaces 534 can be constructed of an elastic or rubber (natural or synthetic) material.

Also, in this embodiment, the support device 514 includes a support member 536 having a release interface 538 and a stopper 540. In the embodiment shown, the support member 536 has a substantially C-shaped, side profile that defines a passageway 542. In this embodiment, the release interface 538 may or may not be configured to be magnetically attracted to the rotor 527.

In an embodiment, the release interface 538 defines a slot configured to receive the peak surface 532 of each one of the coupler portions 528. For example, the slot can have a T-shape that conforms to (and is slightly larger than) a T-shaped peak surface 432. In this way, each peak surface 432 serves as a male element. The slot of the release interface 538 serves as a female element configured to receive and mate with the male elements. As the rotor 527 rotates, the coupler portions 528 travel along an arc and slide within such slot. While within such slot, the release interface 538 restrains the movement of the coupler portions 528 to a circular path of movement, preventing the rotor 527 from decoupling from the support device 514.

As illustrated in FIGS. 27-28, during the pass-through preparation method, in order to pass a cord segment or loop segment 178 of the looped cord 172 between the coupler portions 528 and the support member 536, the user routes the loop segment 178 around the rotor 527, through the C-shaped or arc-shaped passageway 542. The valley space 537 between each coupler portion 528 includes at least part of the passageway 542. In this process, the loop segment 178 fits at least partially within one of the valley spaces 537 while pushing against one of the peak surfaces 532. It should be understood that the cord segment or loop segment 178 can pass by coupler portion 528 to coupler portion 528, sequentially moving from valley space 537 to valley space 537 while traveling through the passageway 542. Alternatively, the user can initially position the loop segment 178 in a first one of the valley spaces 537. The loop segment 178 can remain in the first valley space 537 while traveling entirely through the passageway 542.

In either case, the user can pull the loop segment 178 from the entry space 548 to the outlet space 550 to fully pass the loop segment 178 through the passageway 542. The periodic pass-through cycles enable the user to conveniently perform the pass-through preparation method. During and after the periodic pass-through cycles, the release interface 538 or stopper 540 retains the rotor 527 within the passageway 542, stopping the rotor 527 from falling to the support surface 140, despite the downward piercing force 188.

Figure 29:
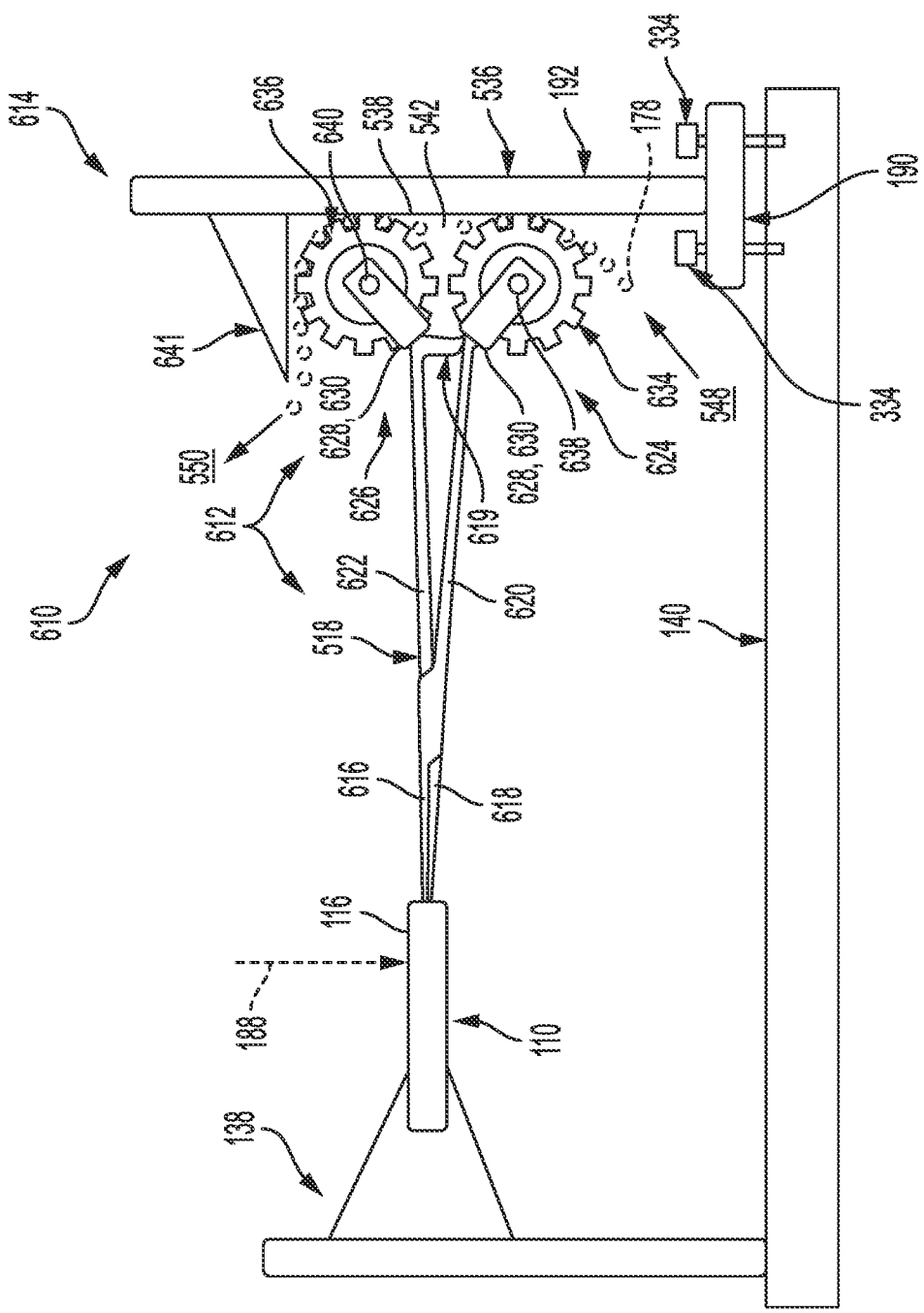
FIG. 29 is a side elevation view of another embodiment of a medical holding system, illustrating a lower rotary coupler, an upper rotary coupler, and the multiple coupler portions of the lower and upper rotary couplers.

In an embodiment illustrated in FIG. 29, the medical holding system 610 includes the same structure, parts, elements and functionality as medical holding system 310 except that the medical holding system 610 includes holder 612 and support device 614. Holder 612 includes: (a) a plurality of jaws 616, 618 pivotally coupled to each other; (b) a position lock 619 configured to secure the jaws 616, 618 in a fixed position that compresses the second element end 116; (c) a plurality of handles 620, 622 connected to the jaws 616, 618, respectively; and (d) a plurality of couplers 624, 626 attached to the handles 620, 622, respectively. Each of the couplers 624, 626 includes a connector 628 having a yoke or fork-shaped frame 630, and shafts 638, 640, each of which is coupled to one of the fork-shaped frames 630. The couplers 624, 626 include wheels or rotors 634, 636. Rotors 634, 636 are rotatably coupled to shafts 638, 640, respectively.

Each of the rotors 634, 636 has the same structure, elements, configuration and functionality as rotor 527 described above with respect to FIG. 28. However, in this embodiment, each of the rotors 634, 636 is configured to be magnetically attracted to the release interface 538 of the support body 192. For example, each of the rotors 634, 636 can include a metallic material configured to be attracted to a release interface 538 that is magnetic or magnetized. In another example, the release interface 538 of the support body 192 can include a metallic material configured to be attracted to the rotors 634, 636, each of which is magnetic or magnetized. In yet another example, the rotors 634, 636 and the release interface 538 can all be magnetic or magnetized to generate an enhanced magnetic attraction force between the rotors 634, 636 and the support body 192.

During the pass-through preparation method, to pass a loop segment 178 between the holder 612 and support device 614, the user routes the loop segment 178 around and behind rotor 634 and then around and behind rotor 636. Referring to FIG. 29, while traveling behind each of the rotors 634, 636, the loop segment 178 fits at least partially within one of the valley space 537 while pushing against the adjacent coupler portion 528. It should be understood that the loop segment 178 can switch from coupler portion 528 to coupler portion 528 while traveling through the passageway 542, or the loop segment 178 can remain in the same valley space 537 of each of the rotors 634, 636. In use, the user pulls the loop segment 178 from the entry space 548 to the outlet space 550 to fully pass the loop segment 178 through the passageway 542. The periodic pass-through cycles enable the user to conveniently perform the pass-through preparation method.

In an embodiment, the support device 614 has a stopper 641, which may or may not be magnetically attracted to the rotors 634, 636. During the periodic passages of the loop segment 178, the stopper 641 retains the rotors 634, 636 engaged with the support body 192. In particular, the stopper 641 prevents the upward force of the loop segment 178 from causing the rotors 634, 636 to fully slide upward and off of the support body 192. During and after the periodic passages of the loop segment 178, the magnetic forces between the rotors 634, 636 and the support body 192 keep the rotors 634, 636 engaged with the support body 192. This prevents the second element end 116 from falling to the support surface 140 despite the downward piercing force 188.

Figure 30:
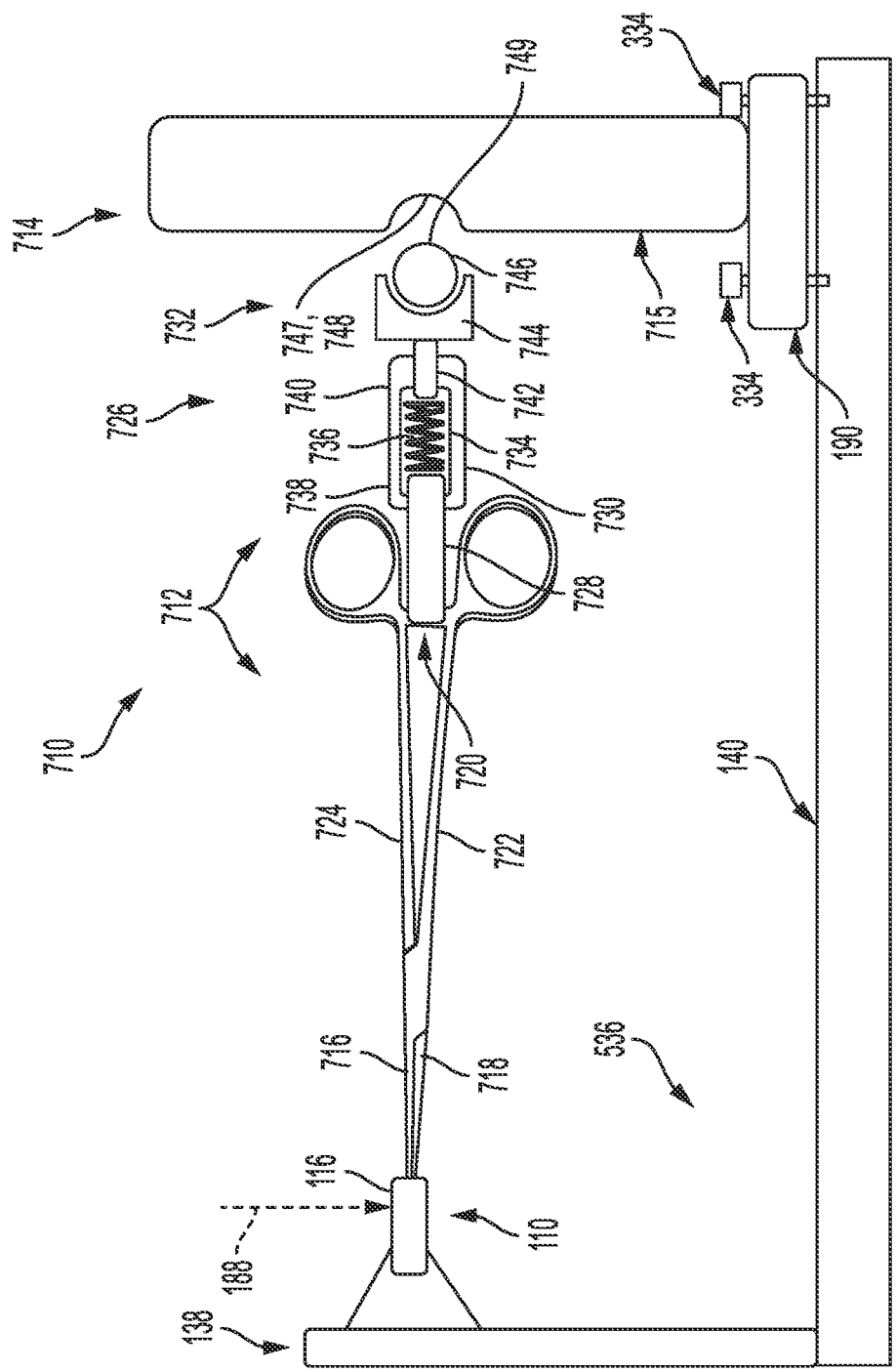
FIG. 30 is a side elevation view of another embodiment of a medical holding system, illustrating a ball-shaped coupler portion uninstalled from a socket of a support device.
Figure 31:
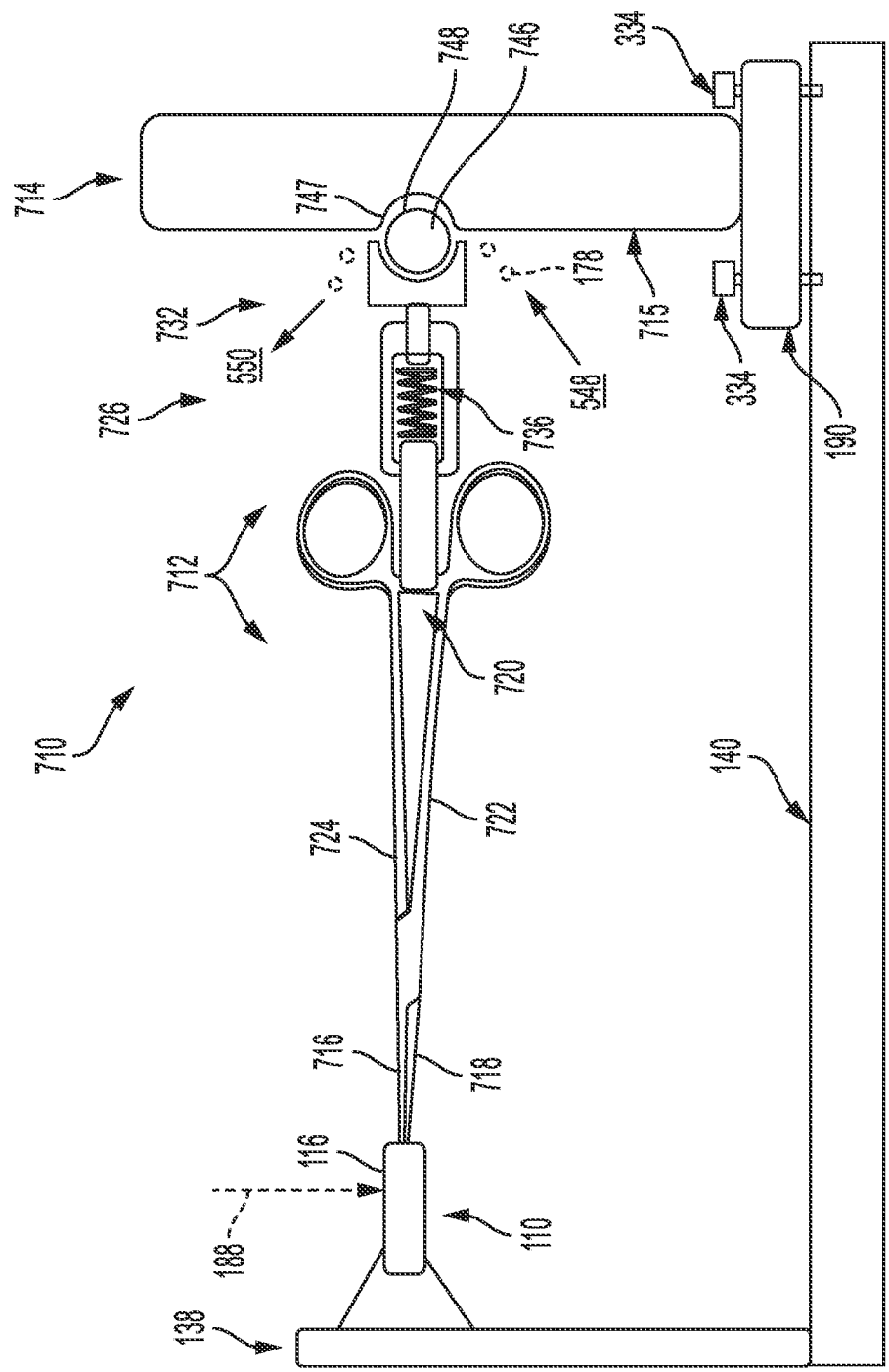
FIG. 31 is a side elevation view of the medical holding system of FIG. 30, illustrating the ball-shaped coupler portion engaged with the socket-shaped release interface of the support device.

In an embodiment illustrated in FIGS. 30-31, the medical holding system 710 includes the same structure, parts, elements and functionality as medical holding system 310 except that the medical holding system 710 includes holder 712, support device 714 and support body 715. Holder 712 includes: (a) a plurality of jaws 716, 718 pivotally coupled to each other; (b) a position lock 720 configured to secure the jaws 716, 718 in a fixed position that compresses the second element end 116; (c) a plurality of handles 722, 724 connected to the jaws 716, 718, respectively; and (d) a coupler 726 connected to the position lock 720.

In the embodiment shown, the coupler 726 includes: (a) a rod or arm 728; (b) a housing 730 configured to receive an end of the arm 728; and (c) a coupler assembly 732. The housing 730 has a retainer 734 configured to hold a biasing member or spring 736. The housing 730 also has a first housing end 738 defining a opening (not shown) configured to receive the arm 728, and the housing 730 has a second housing end 740 defining an opening (not shown) configured to receive an arm 742 of the coupler assembly 732.

The coupler assembly 732 includes: (a) a socket 744; (b) a coupler portion 746 held by the socket 744; and (c) the arm 742 extending from the socket 744. In the embodiment shown, the coupler portion 746 is a joint member. The coupler portion 746 can be a metallic or magnetized ball, or a disk, gear, wheel, rotor or other suitable type of articulating element.

The support body 715 has the same structure, elements and functionality as support body 192 except that support body 715 includes a release interface 747. The release interface 747 defines a socket, slot, groove, recess or cavity 748. The cavity 748 is concave and has an arc shape or partial spherical shape. The cavity 748 is configured to partially receive the coupler portion 746.

In this embodiment, the coupler portion 746 is configured to be magnetically attracted to the support body 715. For example, the coupler portion 746 can include a metallic material configured to be attracted to the support body 715 that is magnetic or magnetized. In another example, the support body 715 can include a metallic material configured to be attracted to the coupler portion 746, which is magnetic or magnetized. In yet another example, the coupler portion 746 and the support body 715 can each be magnetic or magnetized to generate an enhanced magnetic attraction force between the coupler portion 746 and the support body 715.

In the setup stage, the user brings the coupler portion 746 into contact with the support body 715 so that the coupler portion 746 partially fits within the cavity 748, as shown in FIG. 31. The magnetic force between the coupler portion 746 and the support body 715 secures the coupler portion 746 partially within the cavity 748.

During the periodic passages of the loop segment 178 during the pass-through preparation method, the coupler portion 746 remains partially within the cavity 748 and engaged with the support body 715. In particular, the release interface 747, serving as a stopper, prevents the upward force of the loop segment 178 from causing the coupler portion 746 to fully slide upward and off of the support body 715. During and after the periodic passages of the loop segment 178, the magnetic force between the coupler portion 746 and the support body 715 keep the coupler portion 746 engaged with the support body 715. This prevents the second element end 116 from falling to the support surface 140 despite the downward piercing force 188. Each time the users passes the loop segment 178 along the rear side 749 (FIG. 30) of the coupler portion 746, the spring 736 flexes (compresses) to facilitate the passage of the loop segment 178.

Figure 33:
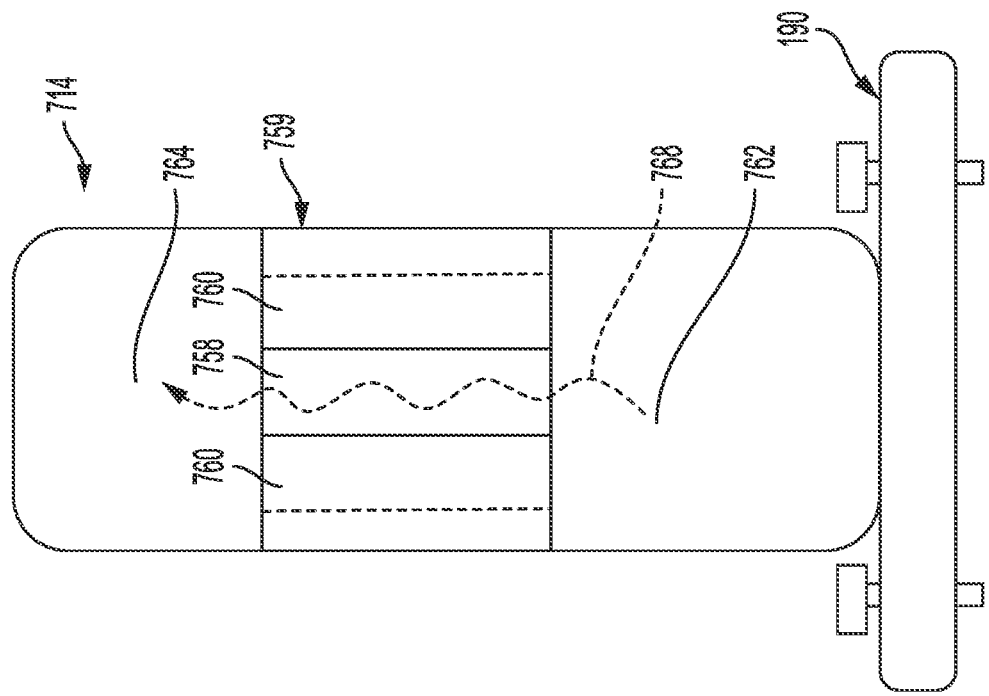
FIG. 33 is a side elevation view of an embodiment of a support device configured for an embodiment of the medical holding system of FIG. 30.
Figure 32:
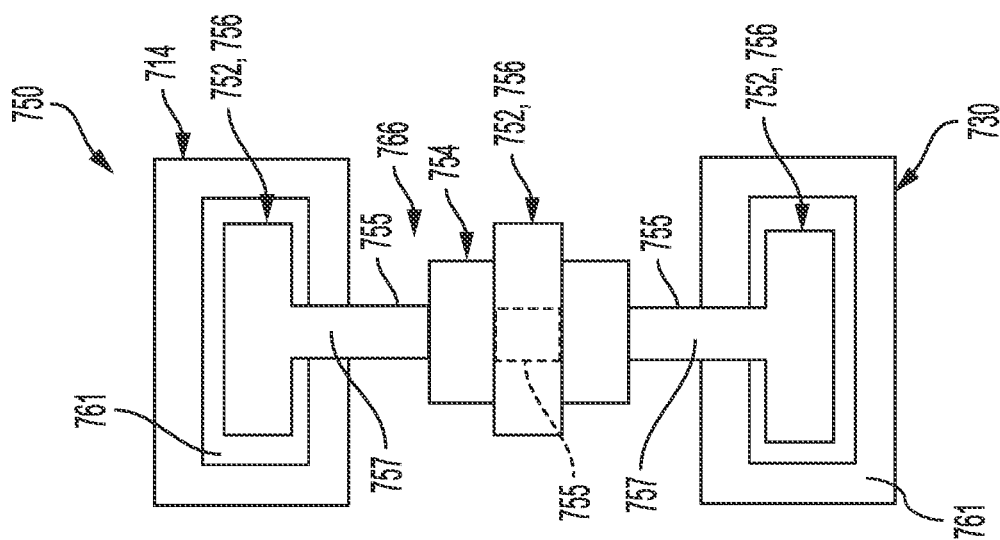
FIG. 32 is a side elevation view of an embodiment of a coupler assembly configured for an embodiment of the medical holding system of FIG. 30.

In another embodiment illustrated in FIGS. 32-33, the coupler 726 includes a coupler assembly 750 in place of the coupler assembly 732. The coupler assembly 750 includes a wheel or rotor that has a plurality of coupler portions 752 that radially extend from the central hub or central portion 754 of the coupler assembly 750. In this example, there are four coupler portions 752, three of which are shown in FIG.

32. The coupler portions 752 are separated by equal angles. Each coupler portion 752 has a neck or extension 755 and a head or retainer member 756. In the example shown, each coupler portion 752 has a T-shape.

The housing 730 defines a first arc-shaped or C-shaped slot 757 configured to receive the extensions 755. The housing 730 also defines a second arc-shaped or C-shaped slot 761 configured to receive the retainer members 756. The first C-shaped slot 757 is narrower than the second C-shaped slot 761. As a result, once a coupler portion 752 rotates within the slots 757, 761, such coupler portion 752 is slidably mated and interlocked with the housing 730. The interlocking enables such coupler portion 752 to slide within the housing 730 while retaining and coupling such coupler portion 752 to the housing 730.

Likewise, the release interface 759 of the support device 714 defines a first arc-shaped or C-shaped slot 758 configured to receive the extensions 755. The release interface 759 also defines a second arc-shaped or C-shaped slot 760 configured to receive the retainer members 756. The first C-shaped slot 758 is narrower than the second C-shaped slot 760. As a result, once a coupler portion 752 rotates within the slots 758, 760, such coupler portion 752 is slidably mated and interlocked with the housing 730. The interlocking enables such coupler portion 752 to slide within the housing 730 while retaining and coupling such coupler portion 752 to the support device 714.

In this embedment, the coupler assembly 750 is positioned between the C-shaped portions of the housing 730 and support device 714. The C-shaped portions of the housing 730 and support device 714 are spaced apart so that there is a lower entry space 762 (FIG. 33) and an upper outlet space 764 (FIG. 33) between such C-shaped portions. When pushed, the central portion 754 is configured to rotate relative to the housing 730 and support device 714. The user can insert the loop segment 178 into a dwelling space 766 (FIG. 32) between two of the extensions 755 and then pull the loop segment 178 upward against a first one of the extensions 752. This causes the central portion 754 to rotate relative to the housing 730 and the support device 714. Eventually, the first extension 752 reaches the upper outlet space 764 and disengages from the release interface 759. This causes the loop segment 178 to fully pass the through the passageway 768. In this example, the passageway 768 includes the space along the arc-shaped path of the first extension 752. At all times during the rotation of the central portion 754, at least one retainer member 756 remains mated with, and slidably interlocked with, the housing 730, and at least one retainer member 756 remains mated with, and slidably interlocked with, the release interface 759. Accordingly, during the rotation action, the support device 714 keeps the implantable element 110 from falling to the support surface 140. The periodic pass-through cycles enable the user to conveniently perform the pass-through preparation method.

Figure 34:
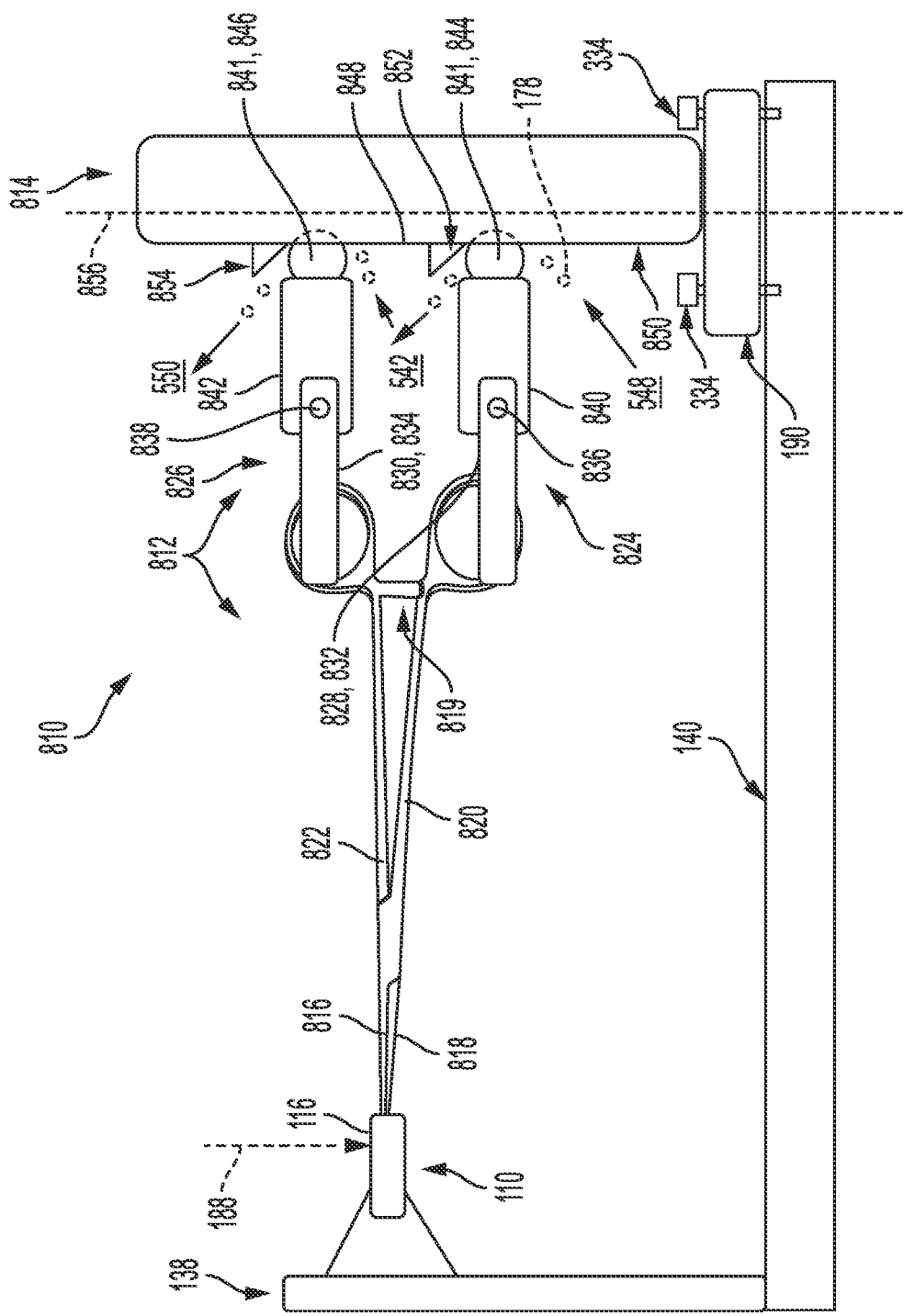
FIG. 34 is a side elevation view of another embodiment of a medical holding system, illustrating a lower rotary coupler that fits within a valley of the support device, an upper rotary coupler that fits within the valley, and the coupler portions of the lower and upper rotary couplers.

In an embodiment illustrated in FIG. 34, the medical holding system 810 includes the same structure, parts, elements and functionality as medical holding system 310 except that the medical holding system 810 includes holder 812 and support device 814. Holder 812 includes: (a) a plurality of jaws 816, 818 pivotally coupled to each other; (b) a position lock 819 configured to secure the jaws 816, 818 in a fixed position that compresses the second element end 116; (c) a plurality of handles 820, 822 connected to the jaws 816, 818, respectively; and (d) a plurality of couplers 824, 826 attached to the handles 820, 822, respectively.

Couplers 824, 826 include: (a) connectors 828, 830 having yokes or fork-shaped frames 832, 834, respectively; (b) shafts 836, 838 coupled to the fork-shaped frames 832, 834, respectively; (c) housings 840, 842 coupled to the frames 832, 834, respectively; and (d) coupler portions 841, 842 coupled to the housings 840, 842. Depending on the embodiment, the each of the coupler portions 841, 842 can include a pivot member, ball, wheel, disk, gear or rotor. In the embodiment shown, the coupler portions 841, 842 include balls 844, 846, respectively. Balls 844, 846 are rotatably mounted within sockets (not shown) defined by the housings 840, 842, respectively. In this embodiment, each of the balls 844, 846 is configured to be magnetically attracted to the release interface 848 of the support body 850. For example, each of the balls 844, 846 can include a metallic material configured to be attracted to the release interface 848 that is magnetic or magnetized. In another example, the release interface 848 of the support body 850 can include a metallic material configured to be attracted to the balls 844, 846, each of which is magnetic or magnetized. In yet another example, the balls 844, 846 and the release interface 848 can all be magnetic or magnetized to generate an enhanced magnetic attraction force between the balls 844, 846 and the support body 850.

In the embodiment shown, the support body 850 includes the release interface 848 and a plurality of stoppers 852, 854. The release interface 848 defines a longitudinal valley extending along the longitudinal axis 856. A portion of each of the balls 844, 846 fits within such valley. The concave shape of the valley enhances the magnetic forces between the balls 844, 846 and the release interface 848.

During the pass-through preparation method, to pass a loop segment 178 between the holder 812 and support device 814, the user routes the loop segment 178 around and behind ball 844 and then around and behind ball 846. The user pulls the loop segment 178 from the entry space 548 to the outlet space 550 to fully pass the loop segment 178 through the passageway 542. The periodic pass-through cycles enable the user to conveniently perform the pass-through preparation method.

It should be understood that the stoppers 852, 854 may or may not be magnetically attracted to the balls 844, 846. During the periodic pass-through cycles of the loop segment 178, the stoppers 852, 854 retain the balls 844, 846 in engagement with the support body 850. In particular, the stopper 852 prevents the upward force of the loop segment 178 from causing the ball 844 to fully slide upward and off of the support body 850, and the stopper 854 prevents the upward force of the loop segment 178 from causing the ball 846 to fully slide upward and off of the support body 850. During and after the periodic passages of the loop segment 178, the magnetic forces between the balls 844, 846 and the support body 850 keep the balls 844, 846 engaged with the support body 850. This prevents the second element end 116 from falling to the support surface 140 despite the downward piercing force 188.

Figure 35:
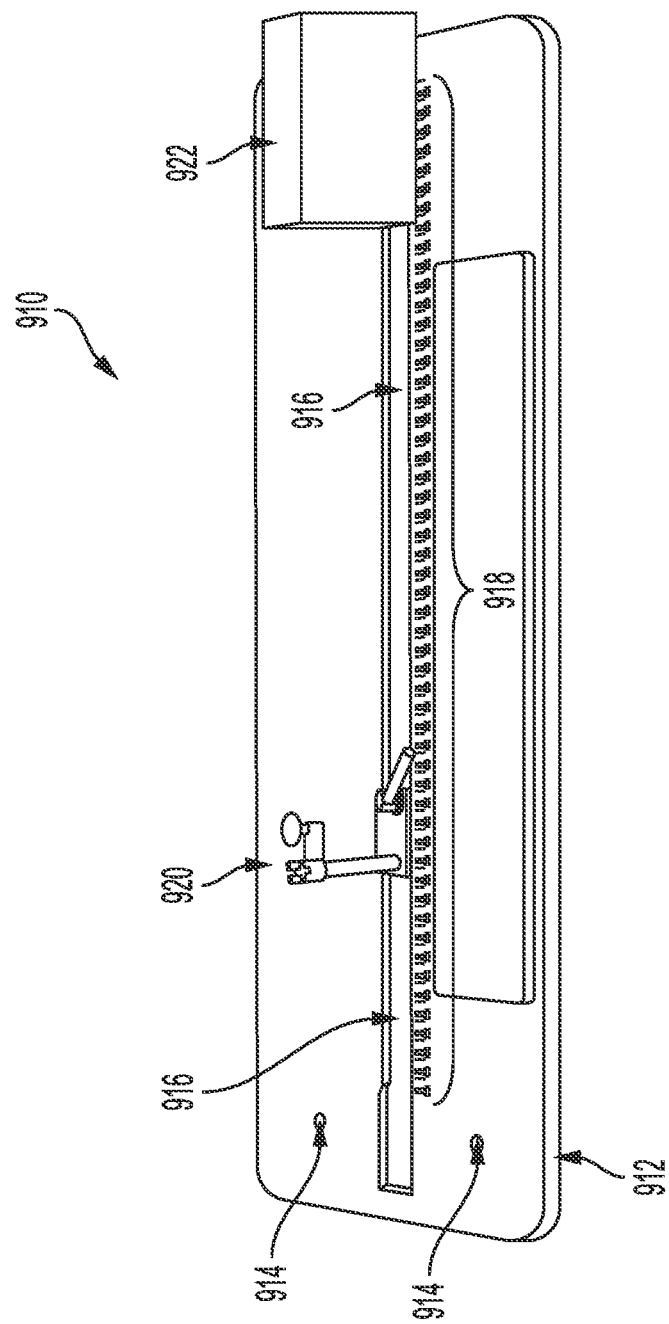
FIG. 35 is an isometric view of an embodiment of an implant preparation station or implant preparation device.

Referring to FIG. 35, in an embodiment, an implant preparation station or implant preparation device 910 includes: (a) a base or support surface 912 defining a plurality of mounting holes 914 and a longitudinal adjustment valley, groove or or track 916; (b) a plurality of measurement markings 918 displayed or otherwise visible adjacent to the track 916; (c) a hanger 920 adjustably coupled to the track 916; and (d) a support device 922 adjustably coupled to the track 916. Depending on the embodiment, the support device 922 can include support device 143, 154, 314, 514, 614, 714, 814 or 922 or any suitable combination thereof. The user can secure the first element end 114 (FIG. 10) to the hanger 920. Next, the user can clamp a holder 141, 152, 312, 512, 612, 712 or 812 (or any suitable combination thereof) onto the second element end 116 (FIG. 10) of an implantable element 110. Next, the user can reversibly couple the applicable holder to the support device 922 according to one of the methods described above. Then, the user can perform the pass-through preparation method, which involves making periodic passes between the support device 922 and such holder which, depending on the embodiment, may be holder 141, 152, 312, 512, 612, 712 or 812 or any suitable combination thereof.

Additional embodiments include any one of the embodiments described above, where one or more of its components, functionalities or structures is interchanged with, replaced by or augmented by one or more of the components, functionalities or structures of a different embodiment described above.

The parts, components, and structural elements of each of the medical holding systems 139, 150, 310, 410, 510, 610, 710 and 810 can be combined into an integral or unitary, one-piece object, or such parts, components, and structural elements can be distinct, removable items that are attachable to each other through screws, bolts, pins and other suitable fasteners. For example, the grasper and coupler can be integral or separate components depending on the embodiment. In another example, the support device and release interface can be integral or separate components depending on the embodiment.

In the foregoing description, certain components or elements have been described as being configured to mate with each other. For example, an embodiment may be described as a first element (functioning as a male) configured to be inserted into a second element (functioning as a female). It should be appreciated that an alternate embodiment includes the first element (functioning as a female) configured to receive the second element (functioning as a male). In either such embodiment, the first and second elements are configured to mate with or otherwise interlock with each other.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The invention claimed is:

1. A medical holding system comprising:
a holder comprising:
(a) a grasper configured to be coupled to an implantable element, wherein the implantable element comprises: (i) a first element end configured to be suspended by a first upright support, wherein the first upright support is configured to be supported by a support surface; and (ii) a second element end, wherein the grasper is configured to be secured to the second element end of the implantable element; and
(b) a coupler comprising at least one coupler portion; and
a support device configured to be coupled to the support surface, wherein the support device comprises a second upright support, wherein the second upright support comprises a release interface,
wherein the at least one coupler portion and the release interface are configured to cooperate with each other so that the at least one coupler portion is configured to be transitioned from an engagement condition to a disengagement condition and back to the engagement condition,
wherein, in the engagement condition the at least one coupler portion is engaged with the release interface to keep the second element end of the implantable element suspended above the support surface when the first element end is suspended above the support surface and the implantable element is subject to a suturing force that acts downward toward the support surface,
wherein, in the disengagement condition, the at least one coupler portion is disengaged from the release interface in response to a pass-through force, thereby providing at least partial access to a passageway, wherein a cord segment of a medical looped cord is configured to be moved through the passageway,
wherein, after the cord segment is moved through the passageway, the coupler portion is configured to transition back to the engagement condition,
wherein, the coupler and the release interface are positioned and configured to keep the implantable element suspended above the support surface throughout a transition between the engagement condition and the disengagement conditions.

2. The medical holding system of claim 1, wherein the grasper comprises a plurality of jaws pivotally coupled together, wherein the jaws are configured to clamp onto the second element end.

3. The medical holding system of claim 1, wherein the implantable element is pierceable by a needle configured to transmit the suturing force.

4. The medical holding system of claim 1, wherein the coupler portion is configured to move between closed and open positions relative to the support device.

5. The medical holding system of claim 4, wherein:
in the closed position, the coupler portion is engaged with the release interface, and the passageway is at least partially closed; and
in the open position, the coupler portion is disengaged from the release interface, and the passageway is temporarily opened.

6. The medical holding system of claim 1, wherein:
the coupler is configured to rotate relative to the support device; and
the at least one coupler portion comprises one of a plurality of coupler portions defined by the coupler, wherein the coupler portions define peaks that are spaced apart from each other, wherein each of the peaks is moveable between a closed position engaged with the release interface and an open position disengaged from the release interface, wherein, throughout the rotation of the coupler, at least one of the peaks comprises the closed position while at least another one of the peaks comprises the open position.

7. The medical holding system of claim 1, wherein:
the coupler comprises a circular shape;
the coupler is configured to rotate relative to the support device;
the at least one coupler portion comprises a first coupler portion of the coupler;
the coupler comprises a second coupler portion separated by the first coupler portion by a valley, wherein the valley is positionable within at least a portion of the passageway;
each of the first and second coupler portions is moveable between a closed position engaged with the release interface and an open position disengaged from the release interface; and
when the first coupler portion comprises the closed position, the second coupler portion comprises the open position.

8. The medical holding system of claim 1, wherein the at least one coupler portion and the release interface are configured to be magnetically attracted to each other.

9. The medical holding system of claim 1, wherein:
the release interface defines a valley; and
the at least one coupler portion at least partially fits within the valley.

10. The medical holding system of claim 1, wherein the coupler and the release interface are configured to keep the implantable element suspended above the support surface throughout the engagement and disengagement conditions without relying on any continuation of any user force.

11. A medical holding system comprising:
a holder comprising:
a grasper configured to be coupled to an end of an implantable element when the implantable element comprises an opposing end coupled to an upright support; and
a coupler comprising at least one coupler portion; and
a support device comprises a release interface, wherein the support device is configured to be supported by a support surface,
wherein the holder and the support device are configured to cooperate with each other so that the at least one coupler portion is configured to transition from an engagement condition to a disengagement condition and back to the engagement condition,
wherein, in the engagement condition, the at least one coupler portion is engaged with the release interface,
wherein, in the disengagement condition, the at least one coupler portion is disengaged from the release interface in response to a force, thereby at least partially providing access to a passageway, wherein a cord segment of a medical cord is moveable along the passageway,
wherein, the holder and the support device are configured to keep the end of the implantable element suspended above the support surface while the opposing end is suspended above the support surface throughout the engagement and disengagement conditions.

12. The medical holding system of claim 11, wherein the grasper comprises a plurality of jaws pivotally coupled together, wherein the jaws are configured to clamp onto the end of the implantable element.

13. The medical holding system of claim 11, wherein the support device comprises a second upright support.

14. The medical holding system of claim 11, wherein:
the at least one coupler portion is configured to move between closed and open positions relative to the support device;
in the closed position, the at least one coupler portion is engaged with the release interface, and the passageway is closed; and
in the open position, the at least one coupler portion is disengaged from the release interface, and the passageway is at least partially temporarily opened.

15. The medical holding system of claim 11, wherein the release interface defines a valley, and the at least one coupler portion comprises a peak configured to fit within the valley.

16. The medical holding system of claim 11, wherein:
the at least one coupler is configured to rotate relative to the support device; and
the at least one coupler portion comprises one of a plurality of coupler portions defined by the coupler, wherein the coupler portions define peaks that are spaced apart from each other, wherein each of the peaks is moveable between a closed position engaged with the release interface and an open position disengaged from the release interface, wherein, throughout the rotation of the coupler, at least one of the peaks comprises the closed position, and at least another one of the peaks simultaneously comprises the open position.

17. The medical holding system of claim 11, wherein the at least one coupler portion and the release interface are configured to be magnetically attracted to each other.

18. The medical holding system of claim 11, wherein:
the release interface defines a C-shaped cavity; and
the at least one coupler portion is configured to at least partially fit within the C-shaped cavity.

19. A medical holding system comprising:
a holder comprising:
a grasper configured to be at least partially coupled to an implantable element, wherein the implantable element comprises: (a) a first end configured to be suspended by an upright support; and (b) a second end, wherein the grasper is configured to be coupled to the second end; and
a coupler comprising at least one coupler portion; and
a support device comprising a release interface, wherein the support device is configured to be supported by a support surface,
wherein the holder and the support device are configured to cooperate with each other so that the at least one coupler portion is configured to be transitioned from an engagement condition to a disengagement condition and back to the engagement condition,
wherein, in the engagement condition, the at least one coupler portion is engaged with the release interface,
wherein, in the disengagement condition, the at least one coupler portion is disengaged from the release interface, thereby at least partially providing access to a passageway, wherein a cord segment of a medical cord is moveable through the passageway,
wherein, when the first end is coupled to the upright support and the second end is coupled to the grasper, the holder and the support device are configured to cooperate with the upright support to keep the second end of the implantable element suspended above the support surface while the first end is suspended above the support surface throughout the engagement and disengagement conditions.

20. The medical holding system of claim 19, wherein:

the grasper comprises a plurality of jaws pivotally coupled together;

the jaws are configured to clamp onto the second end of the implantable element;

the coupler is configured to be at least partially rotated relative to the support device;

the upright support and the support device each extend, at least partially, along a plane; and during the suspension of the implantable element, the implantable element extends, at least partially, along an axis that intersects with the planes.

* * * * *